US012613185B2

(12) United States Patent
    Alam et al.

(10) Patent No.: US 12,613,185 B2
(45) Date of Patent: Apr. 28, 2026

(54) GEMSTONE MULTI-TESTER INSTRUMENT WITH REMOVABLE PROBE

(71) Applicant: Smart Pro Instrument Co., Ltd., Samut Sakhon (TH)

(72) Inventors: Mehboob Alam, Bangkok (TH); Absalon James Montilla, Samut Sakhon (TH); Raweerat Homyamyen Montilla, Samut Sakhon (TH)

(73) Assignee: Smart Pro Instrument Co., Ltd. (TH)

( * ) Notice: Subject to any disclaimer, the term of this patent is extended or adjusted under 35 U.S.C. 154(b) by 0 days.

(21) Appl. No.: 18/220,357

(22) Filed: Jul. 11, 2023

(65) Prior Publication Data

US 2024/0027335 A1     Jan. 25, 2024

Related U.S. Application Data

(63) Continuation-in-part of application No. 18/077,963, filed on Dec. 8, 2022.

(Continued)

(51) Int. Cl.
    *G01N 21/33* (2006.01)
    *G01N 1/44* (2006.01)
    (Continued)

(52) U.S. Cl.
    CPC .............. *G01N 21/33* (2013.01); *G01N 1/44* (2013.01); *G01N 25/18* (2013.01); *G01N 27/041* (2013.01);
    (Continued)

(58) Field of Classification Search
    CPC .......... G01N 21/33; G01N 1/44; G01N 25/18; G01N 27/041; G01N 33/389;
    (Continued)

(56) References Cited

U.S. PATENT DOCUMENTS

| 5,955,735 | A |   | 9/1999 | Coleman |          |
| 6,043,742 | A | * | 3/2000 | Austin  | ................. G01N 33/389 |
|           |   |   |        |         | 702/155  |

(Continued)

OTHER PUBLICATIONS

PCT/IB23/00396, International Search Report & Written Opinion, mailed Oct. 12, 2023.

(Continued)

*Primary Examiner* — Michelle M Iacoletti
*Assistant Examiner* — Maher Yazback
(74) *Attorney, Agent, or Firm* — Aldo Noto, Esq.; Rimon PC

(57)            ABSTRACT

An apparatus (100) for identifying precious stones and man-made stones is disclosed. The apparatus (100) includes a handheld device (2) with a probe (4), a thermal and optical testing assembly, a microcontroller (36), and a visual indicator (6). The probe is electronically coupled with the handheld device (2) and is removable and replaceable. The probe (4) includes a copper tube (5*a*) with an optical fiber (23) and a tip (5) for contacting the stone under test. The thermal testing assembly heats the copper tube (5*a*) and the optical assembly illuminates the stone (12, 13) under test with UV light. The microcontroller (36) determines heat transfer and determines at least one of: the electrical, thermal, and optical properties of the stone. The microcontroller (36) identifies the type of stone, and the visual indicator displays the result.

24 Claims, 28 Drawing Sheets

Related U.S. Application Data

(60) Provisional application No. 63/480,776, filed on Jan. 20, 2023, provisional application No. 63/390,686, filed on Jul. 20, 2022.

(51) Int. Cl.
  *G01N 25/18* (2006.01)
  *G01N 27/04* (2006.01)
  *G01N 33/00* (2006.01)

(52) U.S. Cl.
  CPC ... *G01N 33/389* (2024.05); *G01N 2201/0221* (2013.01); *G01N 2201/062* (2013.01); *G01N 2201/08* (2013.01)

(58) Field of Classification Search
  CPC ..... G01N 2201/0221; G01N 2201/062; G01N 2201/08; G01N 21/87
  See application file for complete search history.

(56) References Cited

U.S. PATENT DOCUMENTS

| | | | | |
|---|---|---|---|---|
| 6,265,884 | B1 * | 7/2001 | Menashi | G01N 27/041 |
| | | | | 324/717 |
| 7,262,835 | B2 * | 8/2007 | Geurts | G01N 21/87 |
| | | | | 356/30 |
| 9,176,068 | B1 | 11/2015 | Radomyshelsky | |
| 2005/0068047 | A1 * | 3/2005 | Claus | G01N 27/221 |
| | | | | 324/693 |
| 2006/0066859 | A1 * | 3/2006 | Downey | G01N 21/431 |
| | | | | 356/445 |
| 2006/0087306 | A1 | 4/2006 | Loginov | |
| 2012/0007619 | A1 | 1/2012 | Zhu et al. | |
| 2014/0337035 | A1 * | 11/2014 | Kessler | G01N 27/041 |
| | | | | 704/274 |
| 2015/0219567 | A1 * | 8/2015 | Sim | G01N 21/87 |
| | | | | 356/30 |
| 2015/0233740 | A1 | 8/2015 | Yeo et al. | |
| 2016/0161420 | A1 | 6/2016 | Zhu et al. | |
| 2016/0161705 | A1 * | 6/2016 | Marquardt | G01J 3/0202 |
| | | | | 356/402 |
| 2020/0110040 | A1 | 4/2020 | Zhu et al. | |
| 2020/0217803 | A1 * | 7/2020 | Tam | G01N 21/59 |
| 2020/0400646 | A1 * | 12/2020 | Tam | G01N 21/8806 |
| 2022/0120695 | A1 | 4/2022 | Zhu et al. | |
| 2023/0129963 | A1 * | 4/2023 | Shibuya | G01N 21/64 |
| | | | | 702/183 |
| 2024/0060879 | A1 * | 2/2024 | Takahashi | G01N 21/33 |
| 2025/0085230 | A1 * | 3/2025 | Tam | G01N 33/389 |

OTHER PUBLICATIONS

PCT/IB23/00417, International Search Report & Written Opinion, mailed Oct. 12, 2023.
PCT/IB2023000396, extended European search report, issued Oct. 2, 2025.
PCT/IB2023000417, extended European search report, issued Oct. 2, 2025.

* cited by examiner

53

5a

23

59

*All measurements are in mm.

⌀5.5

⌀1

⌀0.5

⌀3

⌀2

SECTION A-A

1800

1

GEMSTONE MULTI-TESTER INSTRUMENT WITH REMOVABLE PROBE

CROSS REFERENCE TO RELATED APPLICATIONS

This application claims the benefit of U.S. provisional Application No. 63/390,686, filed Jul. 20, 2022, for DIAMOND AND COLORLESS GEMSTONE MULTI-TESTER; U.S. application Ser. No. 18/077,963, filed Dec. 8, 2022, for DIAMOND AND COLORLESS GEMSTONE MULTI-TESTER; and U.S. provisional Application No. 63/480,776, filed Jan. 20, 2023, for DIAMOND AND COLORLESS GEMSTONE MULTI-TESTER WITH REPLACEABLE PROBE, which are herein incorporated by reference in their entirety. Also, PCT Application No. PCT/IB2023/000396, filed concurrently herewith, for GEMSTONE MULTI-TESTER INSTRUMENT, is hereby incorporated by reference herein in its entirety.

TECHNICAL FIELD

Various embodiments of the disclosure relate generally to testers for the identification of precious stones and man-made stones. More specifically, various embodiments of the disclosure relate to gem testers for distinguishing gemstone such as diamond, moissanite, cubic zirconia, sapphire, ruby, emerald, jade, and synthetic diamond CVD/HPHT, and metals based upon physical conductivity properties, optical properties, and electrical properties.

BACKGROUND

Gemstones such as Cubic Zirconia (CZ), white Sapphire, synthetic Moissanites, and Natural Diamonds have similar physical properties that are hard to differentiate by the human naked eye. This similarity has led to fraudulent practices in which fake stones are combined with real diamonds to maximize profits. To combat such fraudulent and mistaken sales, an advanced gem tester capable of authenticating Natural Diamonds is required.

Diamonds have been cherished as gemstones since ancient times due to their scarcity, hardness, and brilliant sparkle, which make them a symbol of status. In addition to their appeal as gemstones, diamonds possess remarkable properties that captivate material scientists and engineers. Diamonds are the hardest known material, chemically inert, and exhibit the highest thermal conductivity at room temperature. Diamonds are also the least compressible and possess the highest stiffness among gem materials. In addition to diamond's unique mechanical properties, its thermal properties are also unusual. In conjunction with diamond's distinctive mechanical properties, its thermal properties exhibit noteworthy characteristics. The robust interatomic bonding within diamond leads to exceptionally low thermal expansion and elevated acoustic frequencies (yielding an exceedingly high Debye temperature of 2220 K). Furthermore, diamond showcases a remarkably low heat capacity at room temperature. Most notably, diamond possesses an exceptionally elevated thermal conductivity at room temperature, surpassing that of metals like silver or copper by more than fivefold. This considerable thermal conductivity imparts diamond with a heightened resistance to thermal shock and thermal lensing phenomena.

The identification and authentication of diamonds are crucial due to the increasing prevalence of synthetic and treated diamonds that closely resemble natural diamonds. High-pressure, high-temperature (HPHT) processes are used to enhance the color of natural diamonds, while chemical vapor deposition (CVD) synthetic diamonds are often sold without disclosure. These synthetic and treated diamonds may be mixed with natural diamonds, leading to unintentional purchases. Traditional methods of verification, such as sending diamonds for lab analysis, can be expensive and excessive relative to the value of the stone.

Diamonds are composed solely of carbon, making them unique among gem materials. Synthetic diamonds were first successfully produced in the mid-twentieth century using a process that allowed the growth of larger, gem-quality diamonds. Additionally, the CVD techniques were developed in the 1980s, enabling the production of high-quality polycrystalline diamond films.

Gem testing laboratories are expected to detect these newer forms of diamonds when they arise. Visual inspection and spectroscopic techniques are employed to identify synthetic and treated diamonds. Moreover, colored diamonds have gained popularity, and HPHT synthetic diamonds can be produced in various fancy colors. The color of natural diamonds can also be altered through HPHT processing, resulting in color enhancement.

Synthetic moissanite, a manufactured form of Silicon Carbide (SiC), used primarily for ornamental and gem purposes. Initially, opaque crystal groups with iridescent properties were prevalent at gem and mineral shows. However, recent advancements led to the synthesis of a transparent variety. While synthetic moissanite closely imitates many of diamond's properties, gemmologists can readily distinguish between the two using basic equipment. Synthetic moissanite exhibits birefringence absent in diamonds and may display near-parallel needles, stringers perpendicular to the table, rounded facet edges, and uni-directional polishing lines differentiating synthetic moissanite from diamond. Gemological properties of synthetic moissanite include a hardness of 9.25, refractive index (RI) ranging from 2.648 to 2.691 with a birefringence of 0.043, uniaxial positive behavior, and a dispersion of 0.104, which is more than twice that of diamond. Specific gravity (SG) of synthetic moissanite is 3.22, compared to diamond's 3.52. Detecting synthetic moissanite can be accomplished through various means, including reflectivity meters and thermal conductivity testers. Synthetic moissanite, like diamond, is a semiconductor material, with minor differences in chemical composition involving small amounts of nitrogen and boron substitution. Synthetic moissanite exhibits high stability in air, even at elevated temperatures, and is inert to most chemicals, except for fluorine, chlorine, molten alkalis, and certain molten metals. Mounting synthetic moissanite presents no issues with in-situ soldering, similar to diamond jewelry. However, may exhibit slightly lower brilliance, higher dispersion, lower specific gravity, higher refractive index, and lower hardness. Both diamond and synthetic moissanite exhibit similar thermal inertia responses, allowing them to react as "diamond" under a thermal probe.

Cubic Zirconia is a synthetic gem material with a cubic crystal structure. The refractive index of Cubic Zirconia ranges from 2.15 to 2.18, slightly lower than diamond's constant refractive index of 2.42. Cubic Zirconia possesses a dispersion of approximately 0.060, greater than diamond's dispersion of 0.044. With a hardness of 7.5 to 8.5 on the Mohs scale, Cubic Zirconia is widely accepted as a synthetic gem material.

Therefore, in the light of foregoing, there exists a need for an advanced gem tester to authenticate Natural Diamonds because of the difficulty in distinguishing gemstones such as Cubic Zirconia, white Sapphire, synthetic Moissanites, and Natural Diamonds based on their physical properties.

SUMMARY

In one embodiment of the present disclosure, an apparatus for identifying precious stones and man-made stones is described. The apparatus includes a handheld device with a probe attached. The probe includes a copper tube containing at least one optical fiber and a tip that makes contact with the surface of the gemstone being tested. The optical fiber emits light towards the gemstone. The handheld device is electronically coupled with the probe. The probe is removable and replaceable. The handheld device includes a thermal testing assembly coupled to the copper tube and configured to provide heat to the copper tube and sense a temperature of the copper tube, and an optical testing assembly configured to generate short and long wavelength UV light and illuminate the stone under test with at least one of the short wavelength UV light and the long wavelength UV light. The handheld device further includes a microcontroller that is coupled to the thermistor and performs calculations to determine the amount of heat transferred and the properties of the gemstone, such as electrical, thermal, and optical properties. The microcontroller identifies the type of gemstone based on these properties and a visual indicator operably coupled to the microcontroller indicates the type of the stone under test.

Additionally, or optionally, the handheld case further comprises a standardized connection, the probe further comprises a complementary standardized connection, and the probe is removably coupled to the handheld device using the standardized connection and complementary standardized connection.

Additionally, or optionally, the standardized connection is a female connection and the complementary standardized connection is male connection. The probe is adapted to be removed from the handheld device without using any external tools. In one embodiment, the standardized connection comprises a universal serial bus (USB) connection.

Additionally, or optionally, the apparatus includes a detection switch configured to detect a contact between the probe and the stone under test. The detection switch comprises one of an electronic mini-switch and a pressure sensitive sensor.

Additionally, or optionally, when the detection switch detects the contact between the probe and the stone under test, the at least one of the short wavelength UV light and the long wavelength UV light are generated.

Additionally, or optionally, the thermal testing assembly comprises a heating element coupled to the copper tube, and configured to provide heat to the copper tube, and a thermistor operably coupled to the copper tube, and configured to sense the temperature of the copper tube.

Additionally, or optionally, the optical testing assembly comprises a UV light emitting diode (LED) source configured to generate at least one of the short wavelength UV light and the long wavelength UV light, and the at least one optical fiber optically coupled to the UV LED source, and configured to illuminate the stone under test with at least one of the short wavelength UV light and the long wavelength UV light.

Additionally, or optionally, the apparatus may test and identify various types of gemstones, including naturally mined diamonds, Type IIa HPHT diamonds, Type IIa CVD diamonds, simulants, and moissanite.

Additionally, or optionally, the apparatus further includes a conductive hand grip attached to the handheld device. The microcontroller utilizes the hand grip and the probe to determine if the gemstone or area being tested is a metal by establishing a closed electrical circuit, thus indicating electrical conductivity of the gemstone.

Additionally, or optionally, to evaluate the electrical properties of the gemstone, the apparatus further includes a set of relays and a voltage multiplier connected to the microcontroller. This setup allows for high voltage electrical conductivity testing of the gemstone.

Additionally, or optionally, the apparatus enables simultaneous performance of high voltage electrical conductivity testing and exposure of the gemstone to short or long wavelength UV light. Thus, allows for the determination of electrical properties of the gemstone. Also, in some alternative embodiments, this allows for the determination of both electrical and optical properties of the gemstone concurrently.

Additionally, or optionally, the microcontroller is configured to determine at least two of the gemstone's properties, such as thermal, optical, and electrical properties, simultaneously.

Additionally, or optionally, the visual indicator may be multiple light sources. A single light source from the multiple light sources may represent more than one type of gemstone.

Additionally, or optionally, the apparatus further includes a speaker connected to the microcontroller to provide audio information. The microcontroller may select the language for outputting the audio information through the speaker.

Additionally, or optionally, the UV LED source includes an SMD package that emits short wavelength UV light between 250 nm and 275 nm and long wavelength UV light between 350 nm and 375 nm.

Additionally, or optionally, the apparatus further includes a Bluetooth transceiver connected to the microcontroller, allowing communication with a smartphone or tablet via Bluetooth.

Additionally, or optionally, the types of gemstones that may be identified using the apparatus include glass or cubic zirconia, as well as emerald, tanzanite, garnet, tourmaline, jade, spinel, ruby, and sapphire.

In one embodiment of the present disclosure, a method is provided for identifying gemstones using a handheld testing apparatus. The method involves coupling a removable probe to the handheld testing apparatus, heating a copper tube within the apparatus using a heating element, sensing the temperature of the copper tube using a thermistor, placing the heated copper tube in contact with the gemstone under test, determining the heat transfer from the copper tube to the gemstone, generating short or long wavelength UV light, illuminating the gemstone with UV light, determining one or more of the gemstone's properties (electrical, thermal, and optical) including based on the heat transfer, identifying the type of gemstone, and indicating the result through a visual indicator.

Various embodiments of the present disclosure provide the apparatus that facilitates several advantages for testing and identifying gemstones. Firstly, the apparatus provides a comprehensive and portable solution with a handheld case and probe, allowing for convenient and on-the-go gemstone analysis. The incorporation of equipment such as heating elements, thermistors, and optical fibers enables accurate measurement of heat transfer, as well as precise detection of electrical conductivity of the gemstone. The use of UV LED sources facilitates the assessment of optical properties. The microcontroller's capabilities allow for simultaneous determination of multiple properties, including electrical, thermal, and optical characteristics, enabling efficient and holistic gemstone analysis. The visual indicator, which may be multiple light sources, offers a clear and intuitive means of communicating the identified gemstone type. Additionally, the apparatus supports multilingual functionality and audio information output, enhancing user convenience and accessibility. The inclusion of a Bluetooth transceiver enables seamless communication with smartphones or tablets, expanding the device's capabilities and data management options. Overall, these features combine to provide a versatile, user-friendly, and technologically advanced gemstone testing and identification apparatus.

BRIEF DESCRIPTION OF THE DRAWINGS

The illustrated embodiments of the subject matter will be best understood by reference to the drawings, wherein like parts are designated by like numerals throughout. The following description is intended only by way of example, and illustrates certain selected embodiments of devices, systems, and processes that are consistent with the subject matter as claimed herein.

6

Figure 11A:
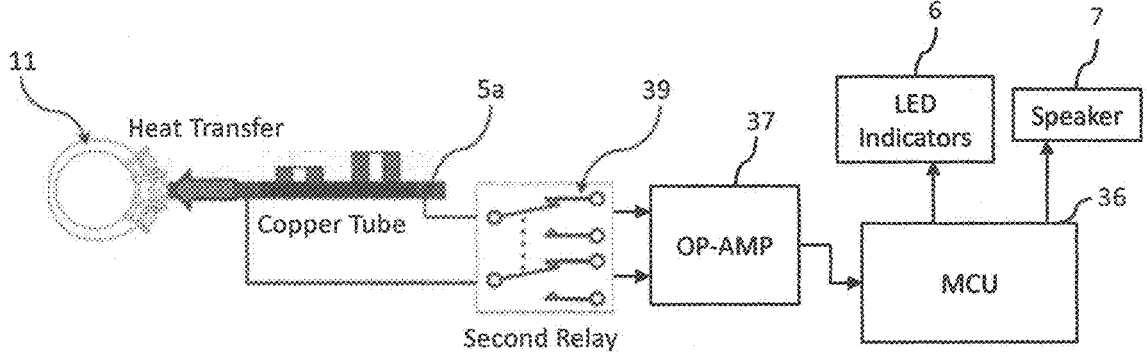
Figure 11B:
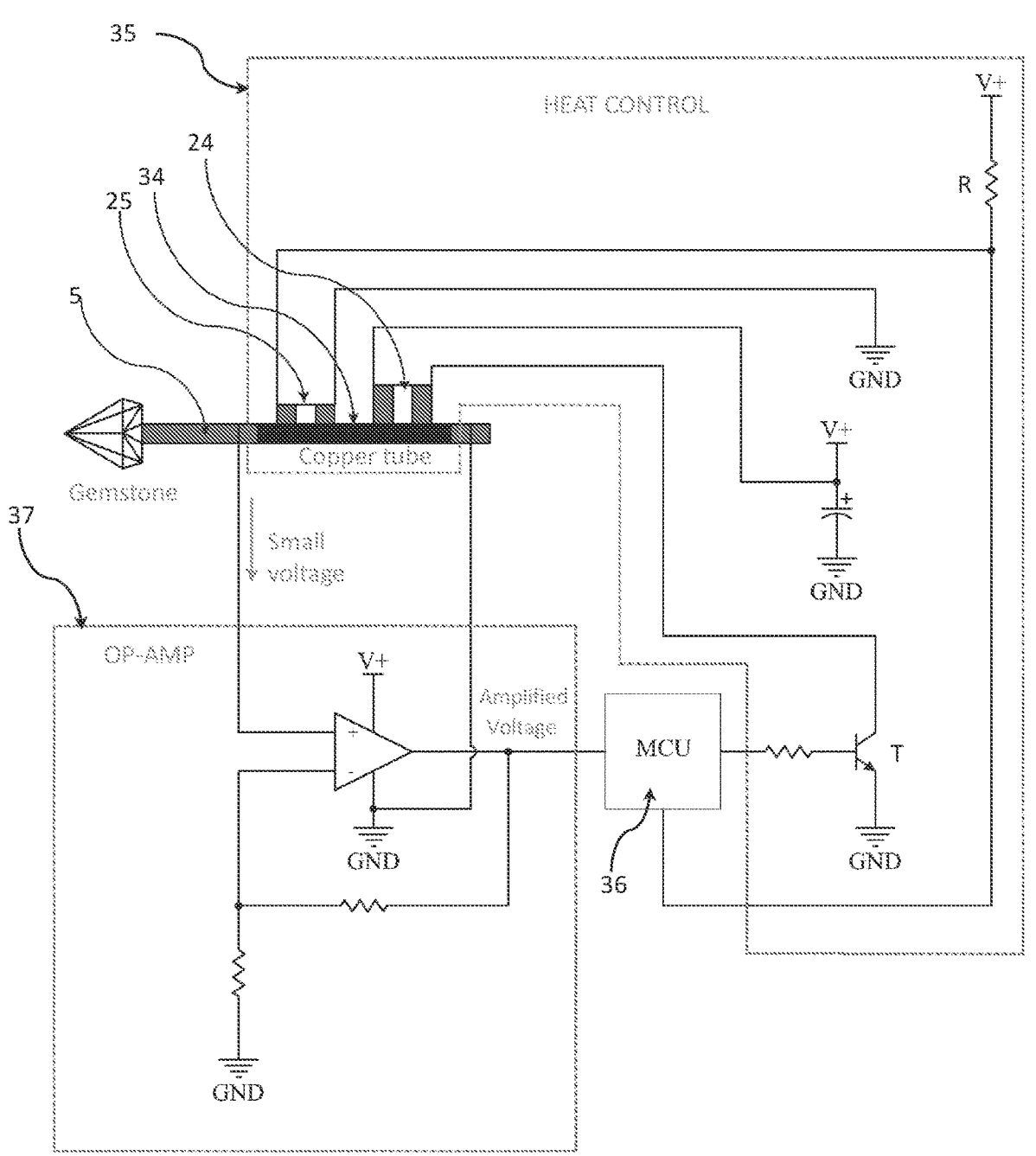
Figure 12:
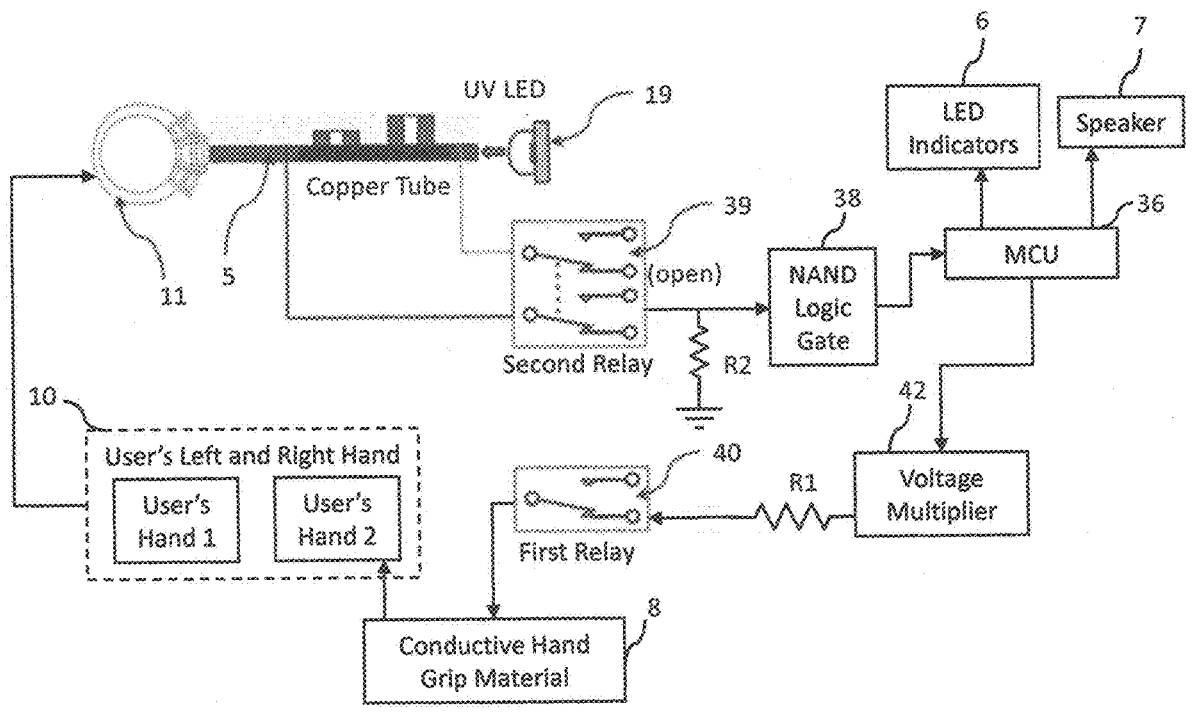
Figures 13A, 13B:
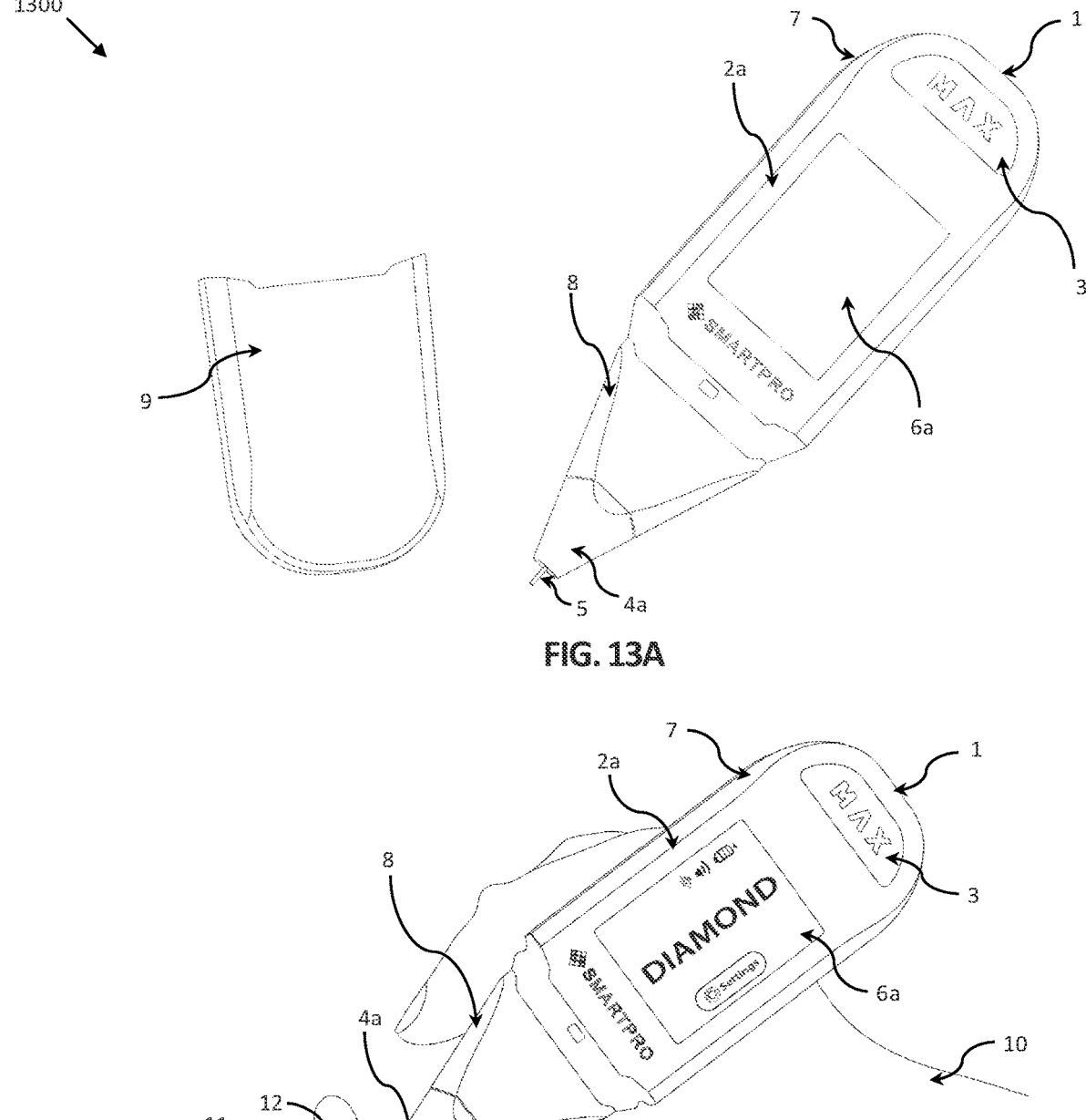
Figure 14A:
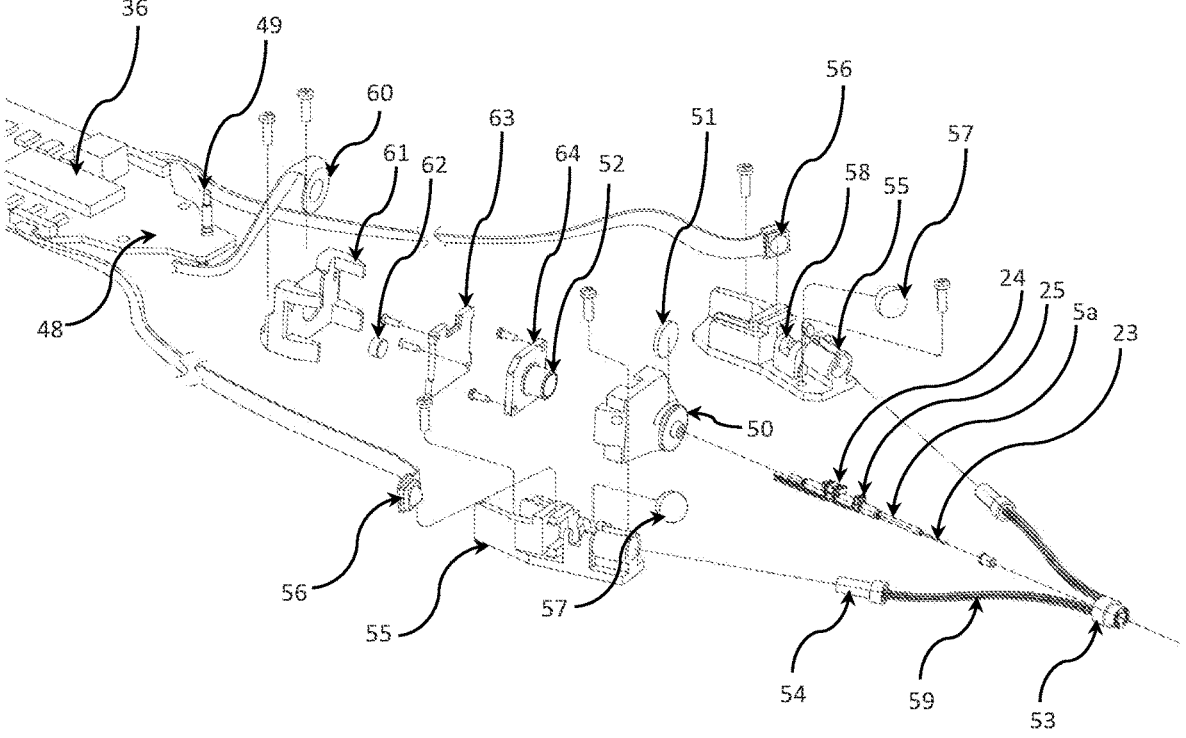
Figure 14B:
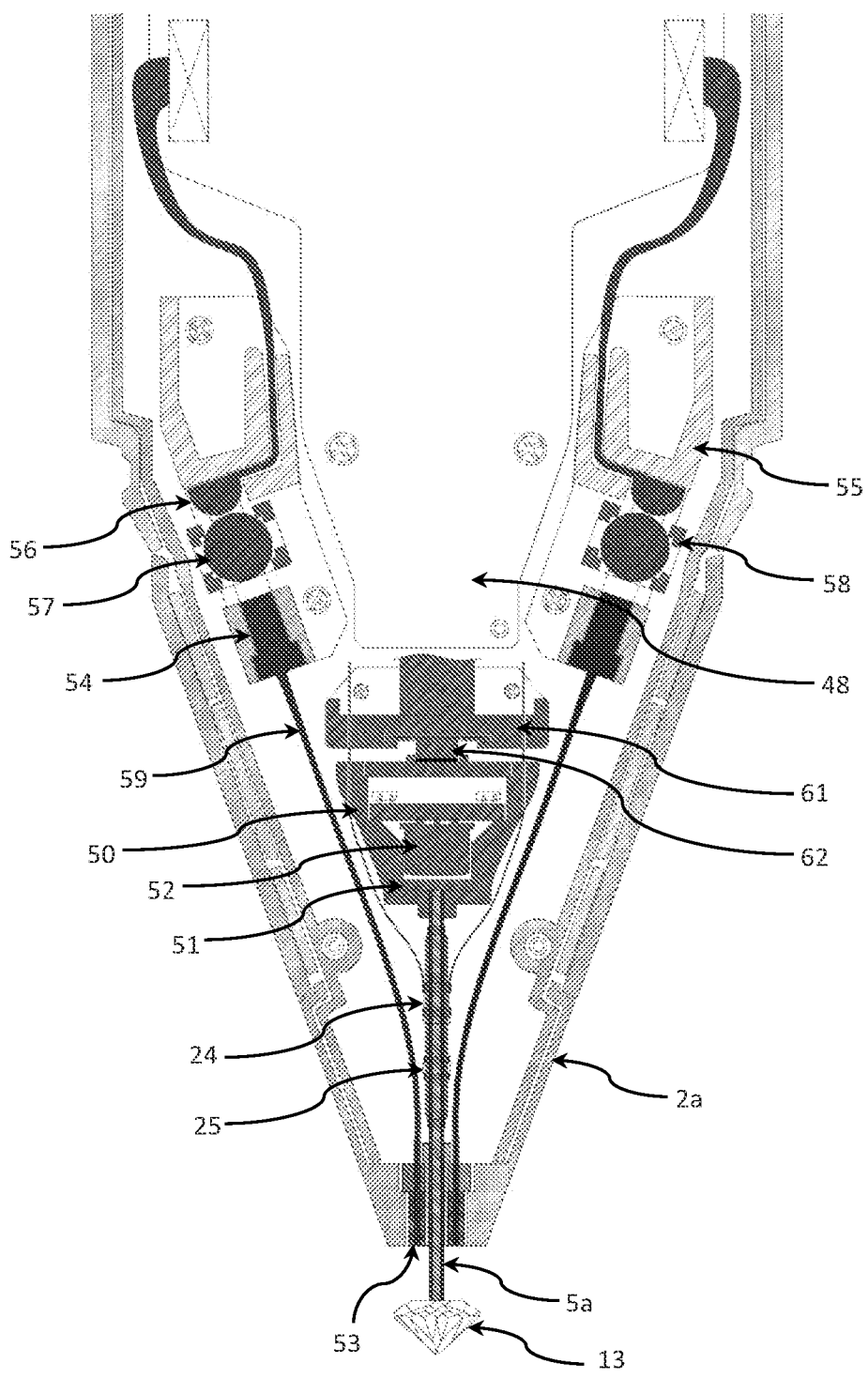
Figure 14C:
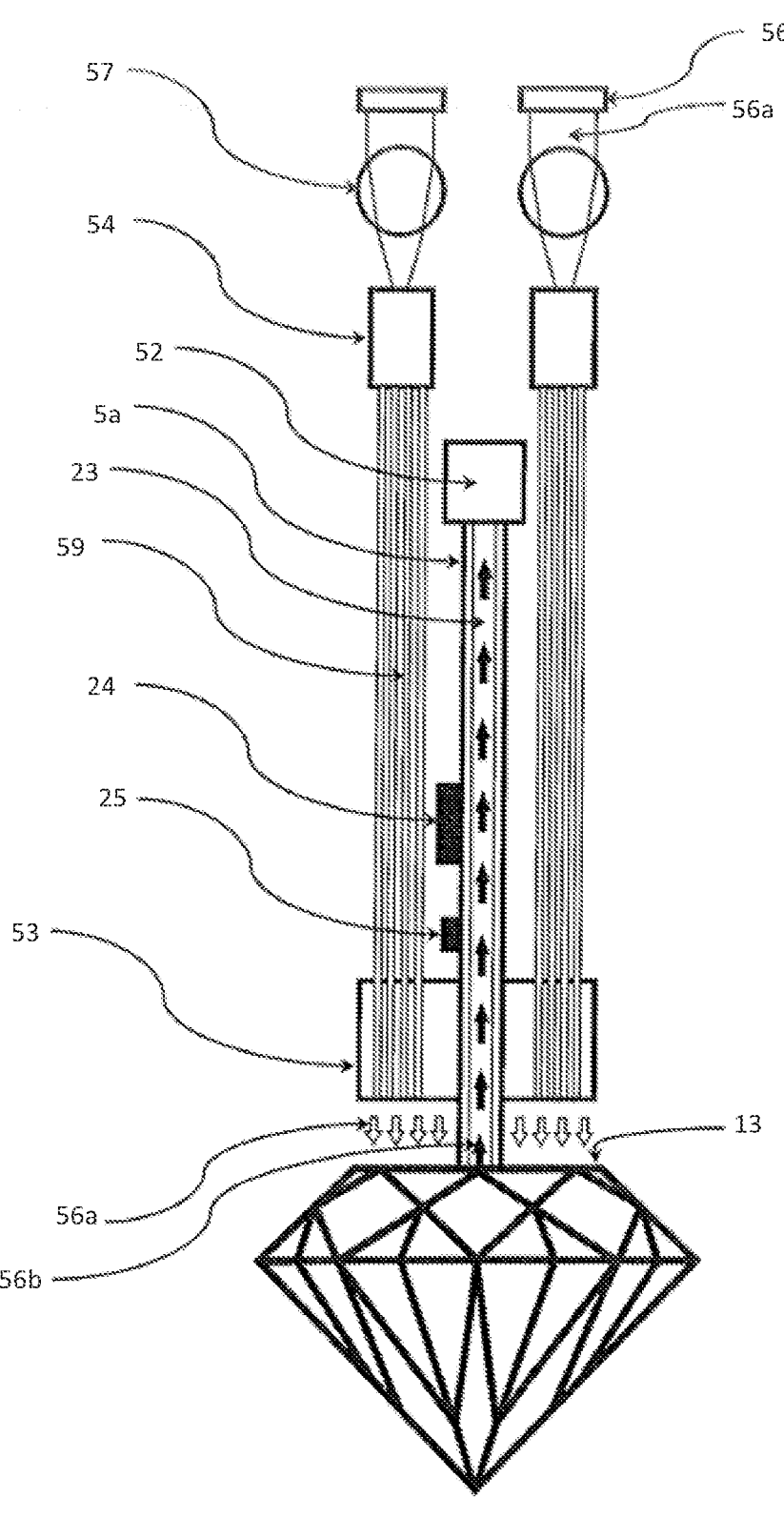
Figure 14D:
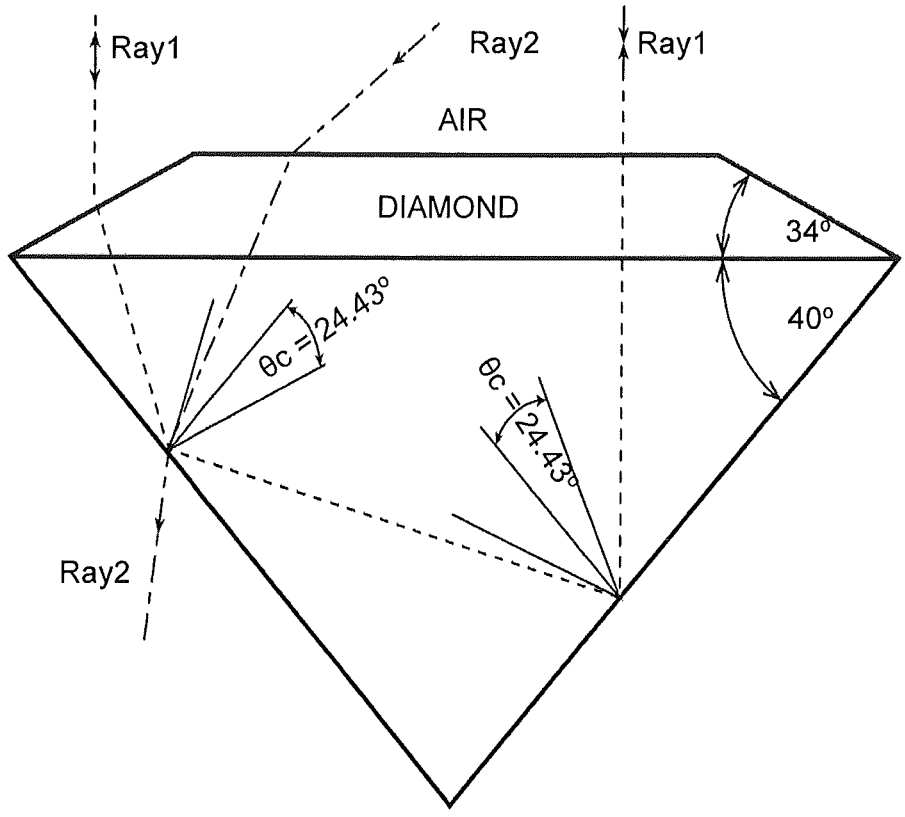
Figure 15A:
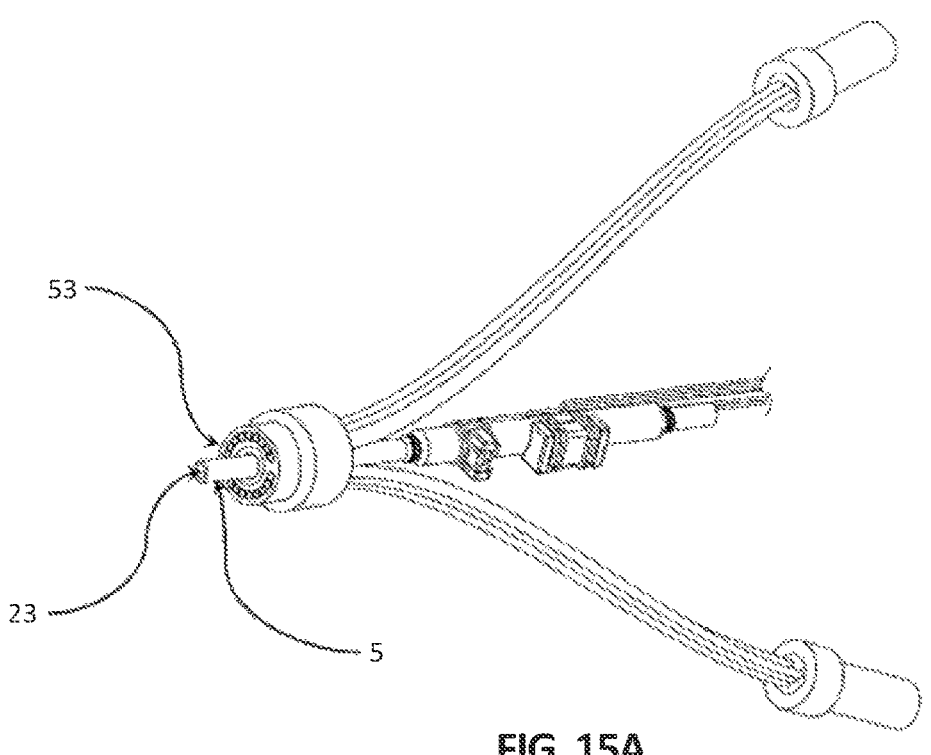
Figure 15B:
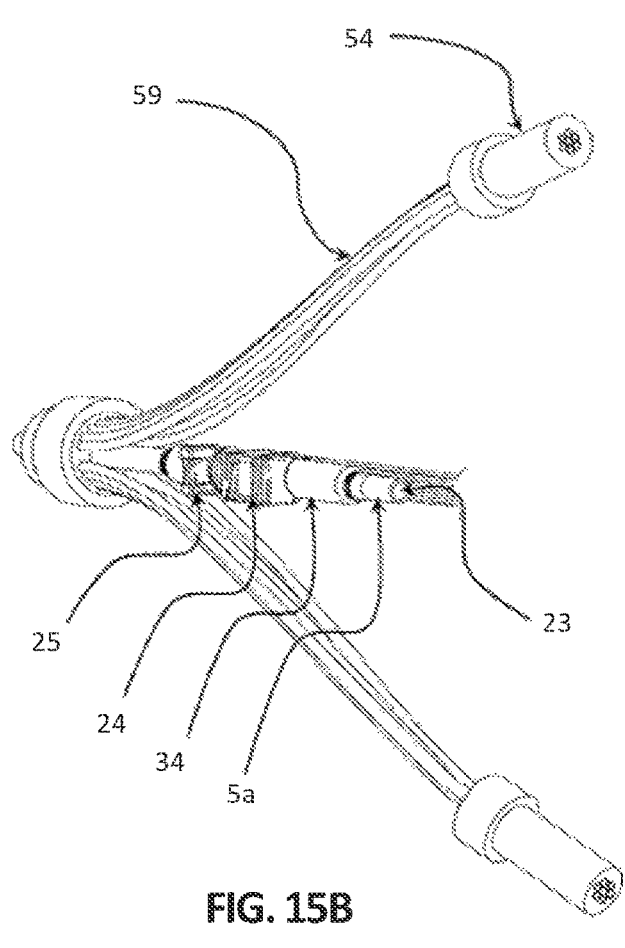
Figure 16A:
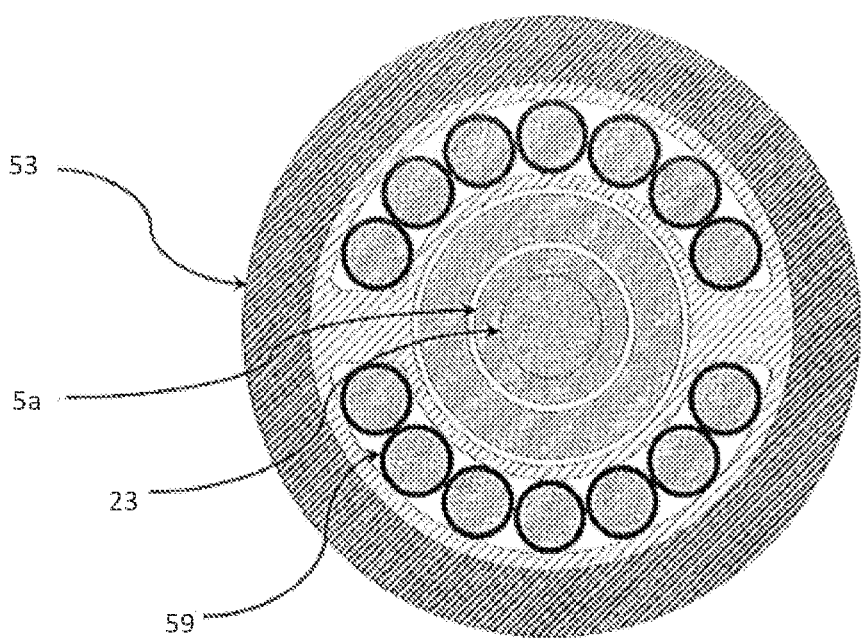
Figure 16B:
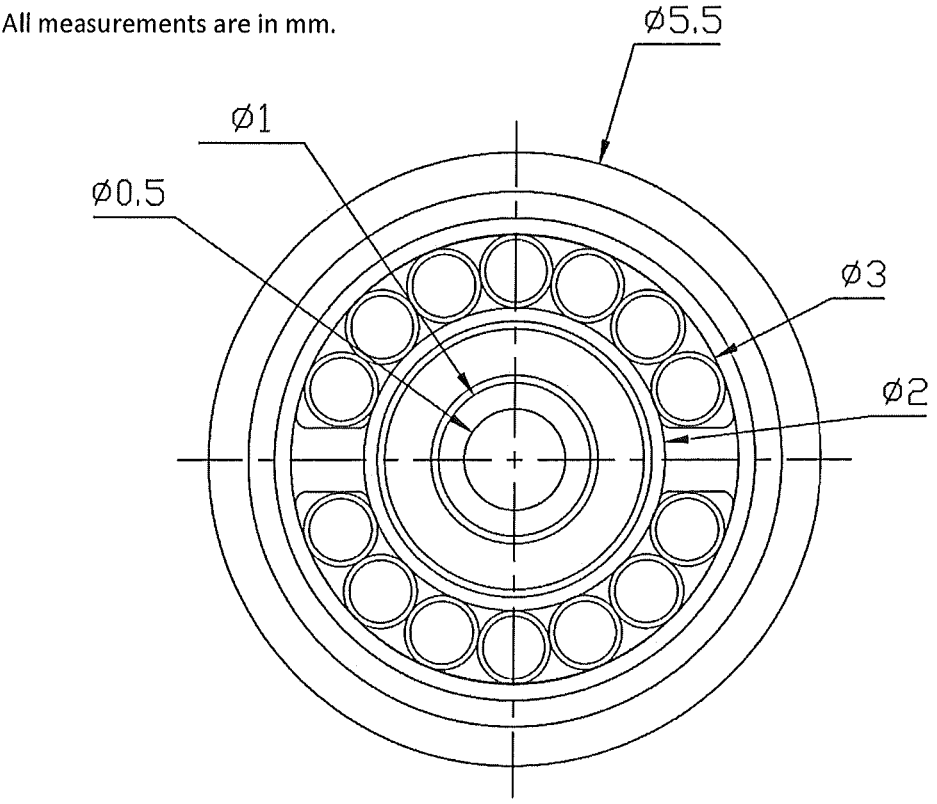
Figures 17A, 17B, 17C:
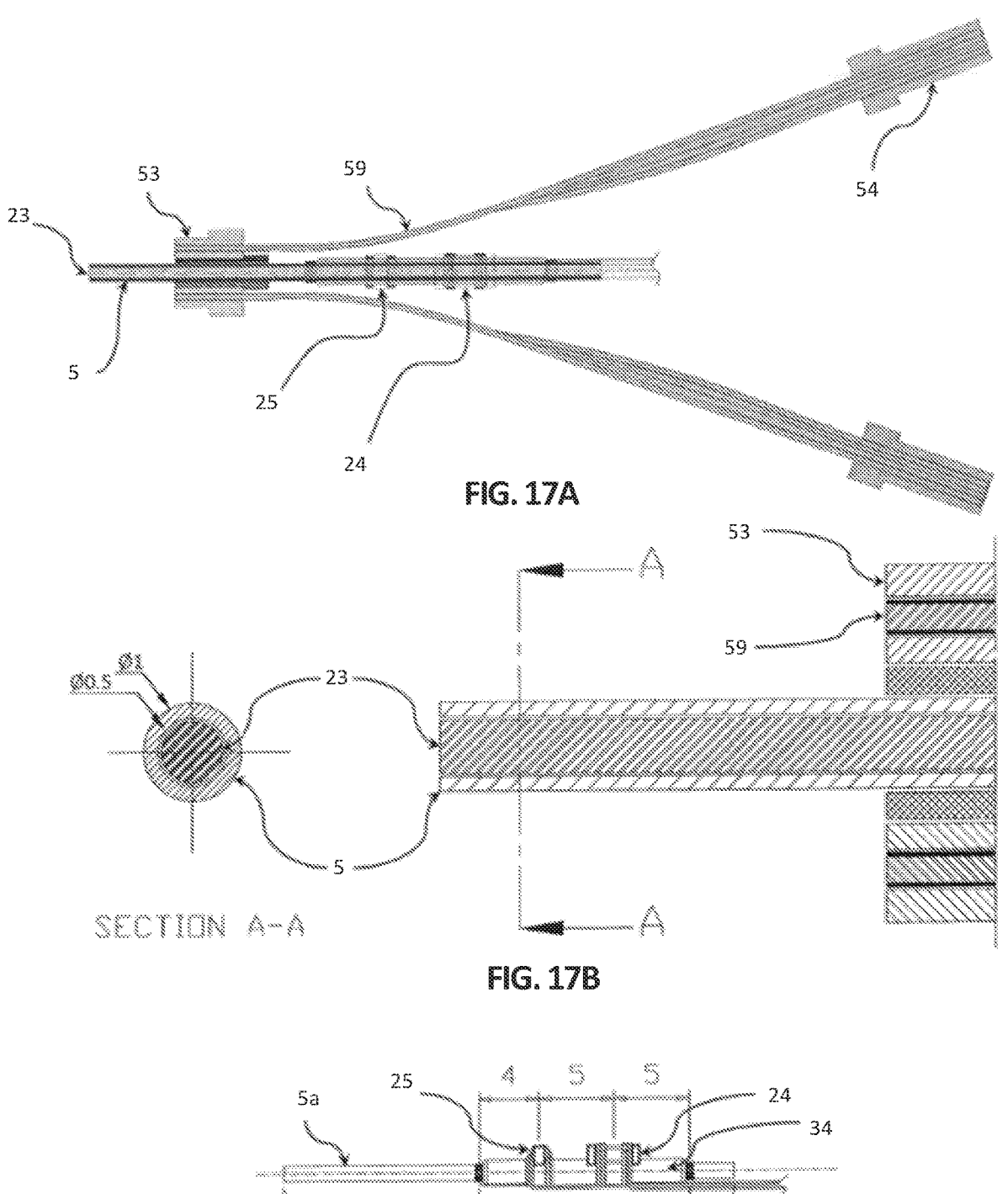
Figure 18A:
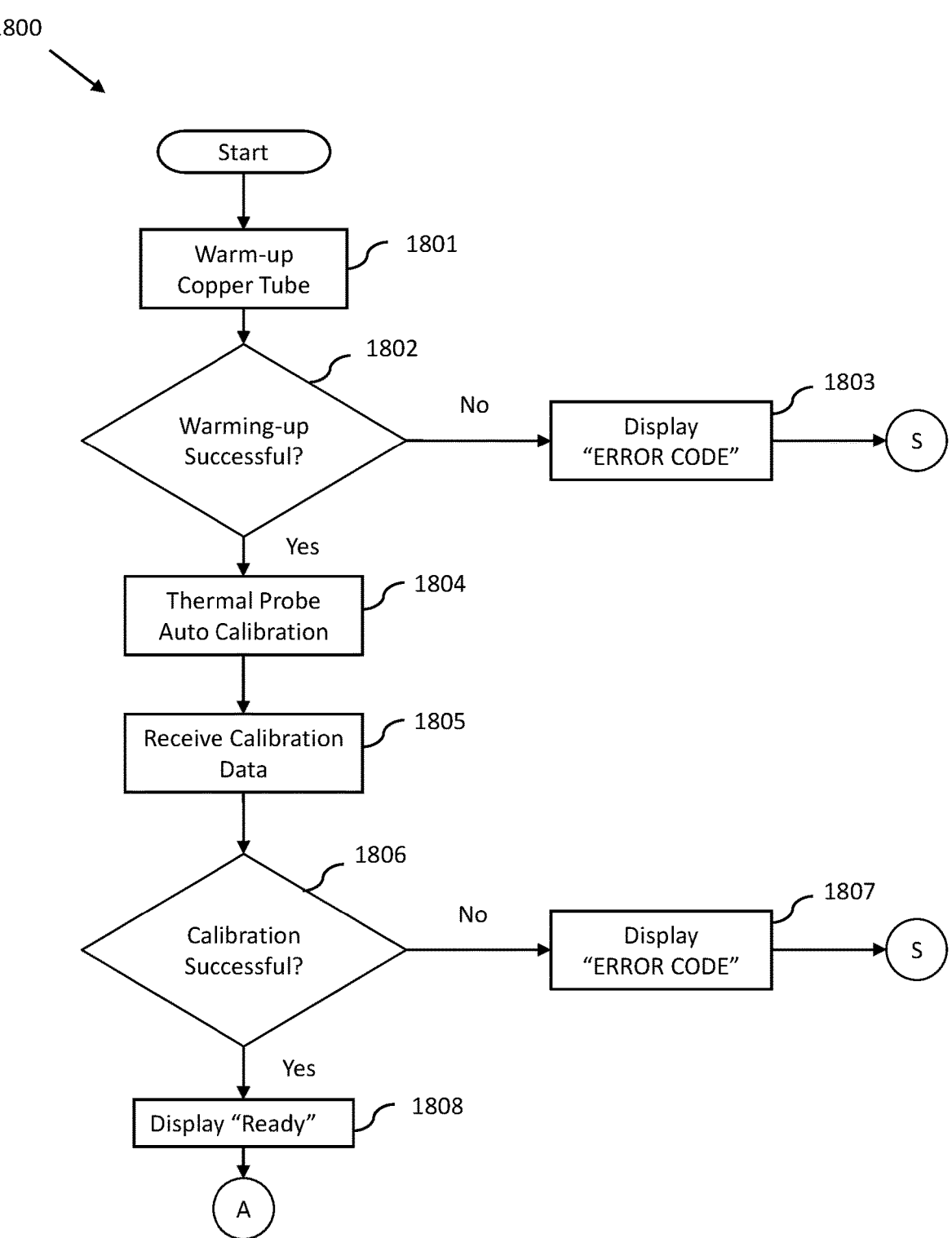
Figure 18B:
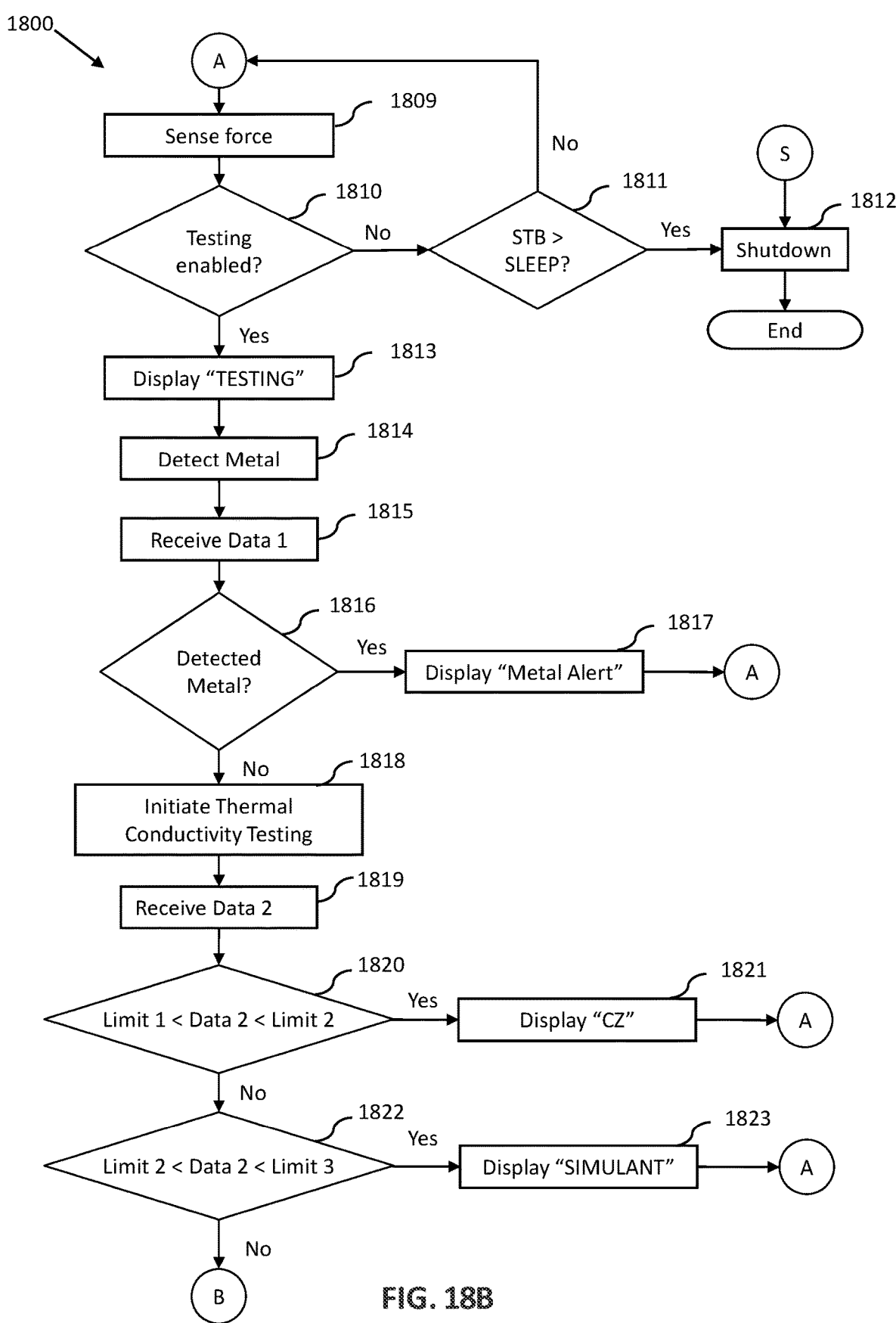
Figure 18C:
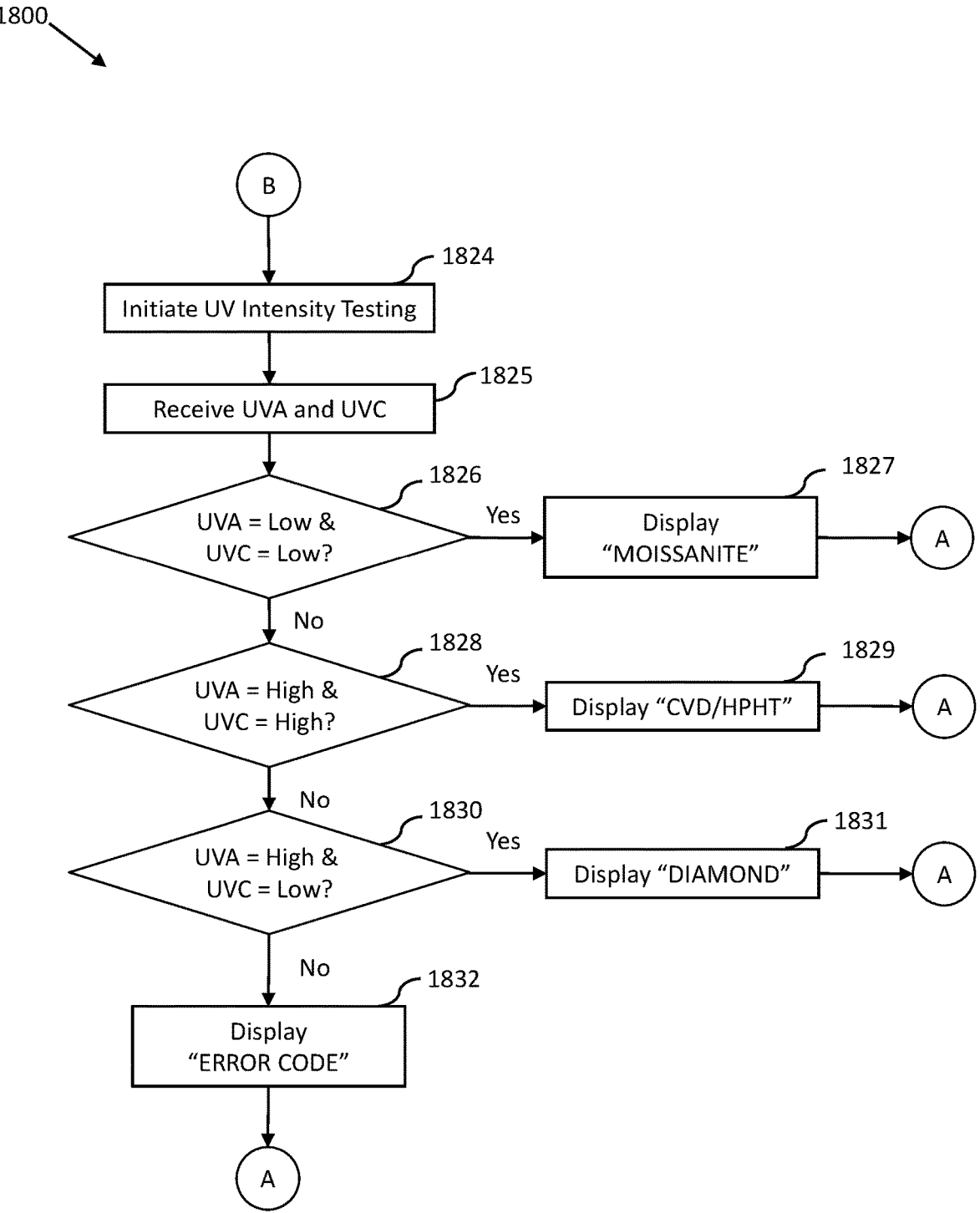
Figure 19:
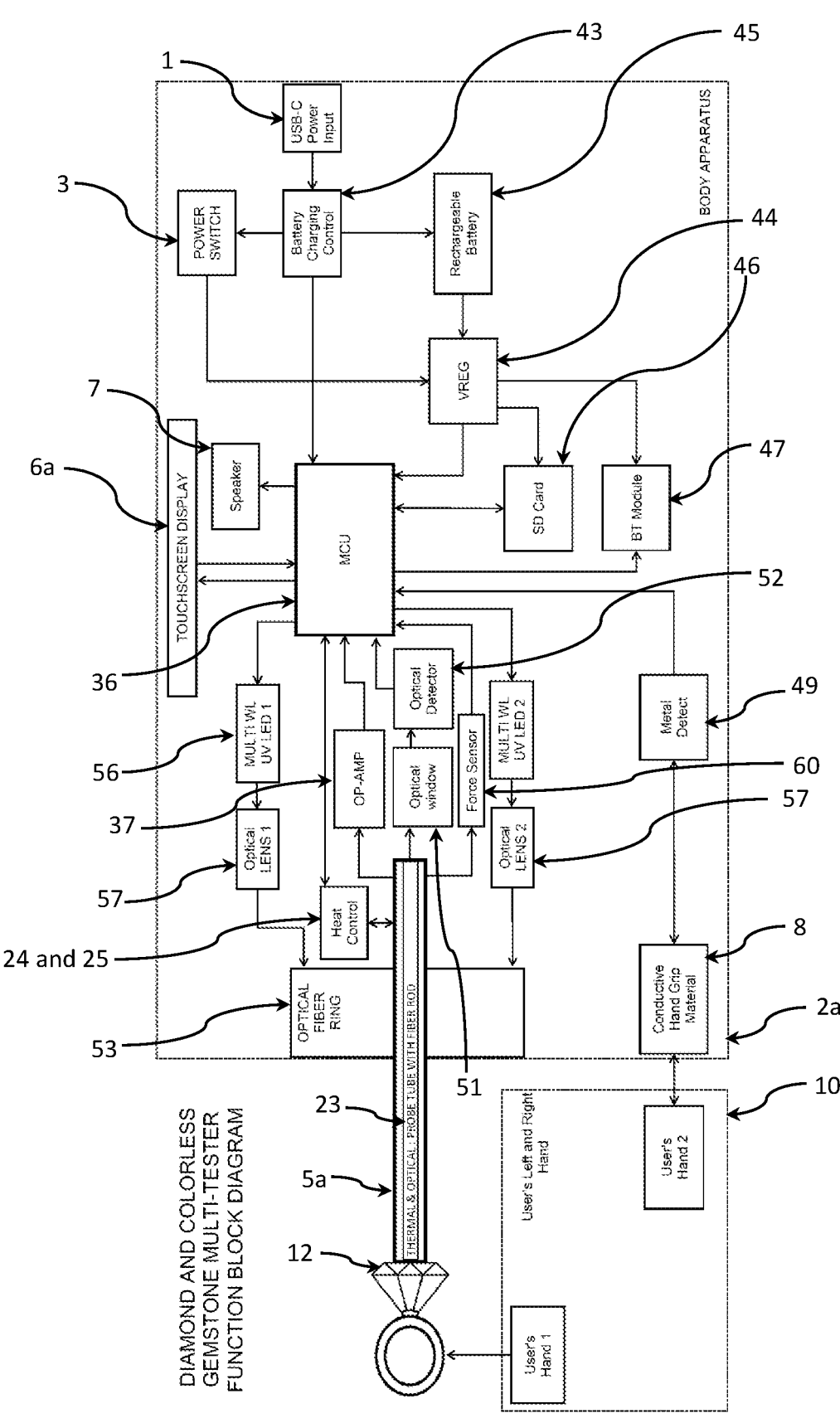
Figure 20:
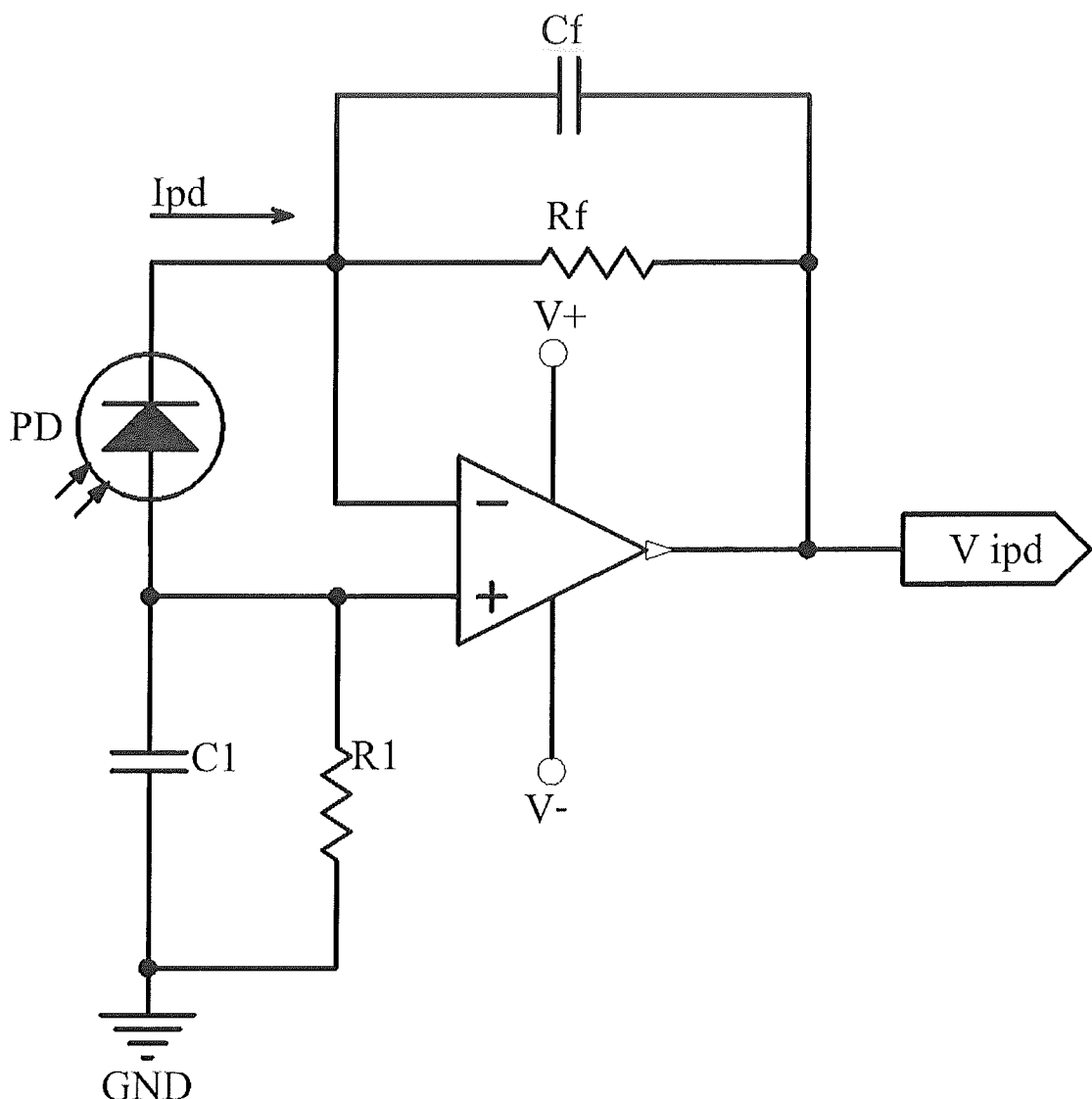

FIG. 11A is a schematic block diagram of the apparatus for testing thermal conductivity, in accordance with an embodiment of the present disclosure;

FIG. 11B is a schematic block diagram of the apparatus for electrical testing, in accordance with an embodiment of the present disclosure;

FIG. 12 is a schematic block diagram of the apparatus for high voltage electrical conductivity test, in accordance with an embodiment of the present disclosure:

FIG. 13A illustrates an apparatus for testing and identifying gemstones, in accordance with another embodiment of the present disclosure;

FIG. 13B is a simulation of an actual testing operation of a mounted gemstone, in accordance with another embodiment of the present disclosure;

FIG. 14A illustrates a partially exploded view of the apparatus, in accordance with another embodiment of the present disclosure;

FIG. 14B illustrates a partial sectional view of the apparatus, in accordance with another embodiment of the present disclosure;

FIG. 14C illustrates an operation of the apparatus for thermal and optical testing, in accordance with another embodiment of the present disclosure;

FIG. 14D illustrates critical angles of a diamond, in accordance with an embodiment of the present disclosure;

FIG. 15A and FIG. 15B illustrate perspective views of an architecture of the testing assembly of the apparatus, in accordance with another embodiment of the present disclosure;

FIG. 16A and FIG. 16B are cross sectional views of the optical fiber bundle head with the optical fiber bundle surrounding the copper tube and the internal optical fiber of the apparatus, in accordance with another embodiment of the present disclosure;

FIG. 17A is cross-sectional view of the probe and an optical fiber bundle assembly, in accordance with another embodiment of the present disclosure;

FIG. 17B is a cross sectional view of the tip of the probe and the optical fiber bundle head, in accordance with another embodiment of the present disclosure;

FIG. 17C is an isometric view illustrating dimensions of the copper tube with the thermistor of the apparatus, in accordance with another embodiment of the present disclosure;

FIGS. 18A-18C, collectively, represent a flow chart illustrating a mode of operation of the apparatus for gemstone testing, in accordance with another embodiment of the present disclosure;

FIG. 19 is a schematic block diagram of the apparatus, in accordance with another embodiment of the present disclosure; and FIG. 20 is a schematic diagram of a pre-amplifier circuit with a low pass filter, in accordance with an embodiment of the present disclosure.

DETAILED DESCRIPTION

Example apparatus are described herein. Other example embodiments or features may further be utilized, and other changes may be made, without departing from the spirit or scope of the subject matter presented herein. In the following detailed description, reference is made to the accompanying drawings, which form a part thereof.

The example embodiments described herein are not meant to be limiting. It will be readily understood that the aspects of the present disclosure, as generally described herein, and illustrated in the drawings, can be arranged, substituted, combined, separated, and designed in a wide variety of different configurations, all of which are explicitly contemplated herein.

A method for measuring a thermal conductivity of gemstones includes sensing the temperature change of a probe tip upon contact with a gemstone. Once the temperature reaches a preset level, a timer circuit is activated, and when it reaches a lower preset level, the timer is deactivated. The digital display indicates the thermal conductivity based on the time interval between the two temperature levels. A shorter time interval corresponds to a higher thermal conductivity and is represented by a smaller readout number.

Light absorption spectra of diamonds are divided into two groups: cape series diamonds and diamonds in the second group. The cape series diamonds fluoresce with a blue light and have a body color ranging from colorless to yellow. The strongest absorption line is observed at 415 nm, accompanied by lines at 478 nm, 465 nm, 452 nm, 435 nm, and 423 nm. The second group of diamonds exhibits a brown, a greenish yellow, or a green body color and illustrate a green response to ultra-violet (UV) light. The second group of diamonds display a strong narrow line at 503 nm and weak lines at 537 nm and 495 nm. Additionally, blue and green fluorescing diamonds may exhibit the 415 nm line. Pink diamonds may show an orange fluorescence with persistent orange phosphorescence, accompanied by bright lines at 575 nm, weaker bands at 586 nm, 598 nm, and 618 nm, and an additional bright line at 537 nm in some cases. The classification of diamonds into types I and II is based on their transparency to UV, with type II diamonds being more transparent and passing UV down to about 225 nm. Type II diamonds are further subdivided into type IIa and type IIb, with the latter exhibiting bluish phosphorescence and electrical conductivity due to the presence of boron atoms.

A refractive index (RI) is an important characteristic for identifying gemstones. Most gemstones have a constant and precise refractive index that may be measured with high accuracy. The refractive index is a measure of the degree by which a material bends or refracts light passing through the material. When light passes from a less dense medium to a denser medium, such as from air to a gemstone, it is refracted towards the normal. The refractive index may be expressed as a ratio of a velocity of light in air to a velocity of light in the gemstone. A critical angle, which is related to the refractive index, determines whether light may get refracted or reflected within a gemstone. Gemstones with high refractive indices exhibit low critical angles, resulting in a higher amount of internal reflection and greater brilliance.

Diamonds, being one of the hardest materials, possess transparency and a high refractive index, which contribute to their brilliance. Total internal reflection and dispersion are responsible for the "shine" and play of light in diamonds. The high refractive index and dispersion value, along with the small critical angle of diamonds allow a significant percentage of incident rays to undergo total internal reflection, maximizing internal reflection within the diamond. The precise cutting and polishing of diamonds ensure straight paths for light rays, enhancing the overall shine.

A gemstone testing apparatus of the present disclosure determines optical properties of gemstones, as well as their thermal conductivity, light absorption spectra, and refractive index, to provide accurate and reliable measurements for identification purposes.

Figure 1A:
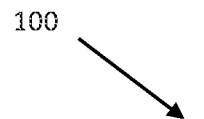
FIG. 1A illustrates an apparatus for testing and identifying gemstones, in accordance with an embodiment of the present disclosure.

FIG. 1A illustrates an apparatus 100 (hereinafter also referred to as "the tester device 100") for testing and identifying gemstones, in accordance with an embodiment of the present disclosure. The tester device 100 (handheld testing apparatus) is powered by a rechargeable battery 1 or a power source 1, for example, a universal serial bus (USB)-C input power. In one embodiment, the tester device 100 includes a handheld body 2, a power switch 3 with status indicator, a replaceable test probe 4 (hereinafter also referred to as "the probe 4") having a probe tip 5, a visual indicator 6, a speaker 7, a conductive hand grip material 8, and a protective cover 9. In one embodiment, the tester device 100 includes open slots for the speaker 7. In the current embodiment, the visual indicator 6 corresponds to light emitting diode (LED) indicators 6 having a plurality of light sources (e.g., LEDs). In one embodiment, a single light source of the plurality of light sources is configured to represent more than one type of stone.

Figure 1B:
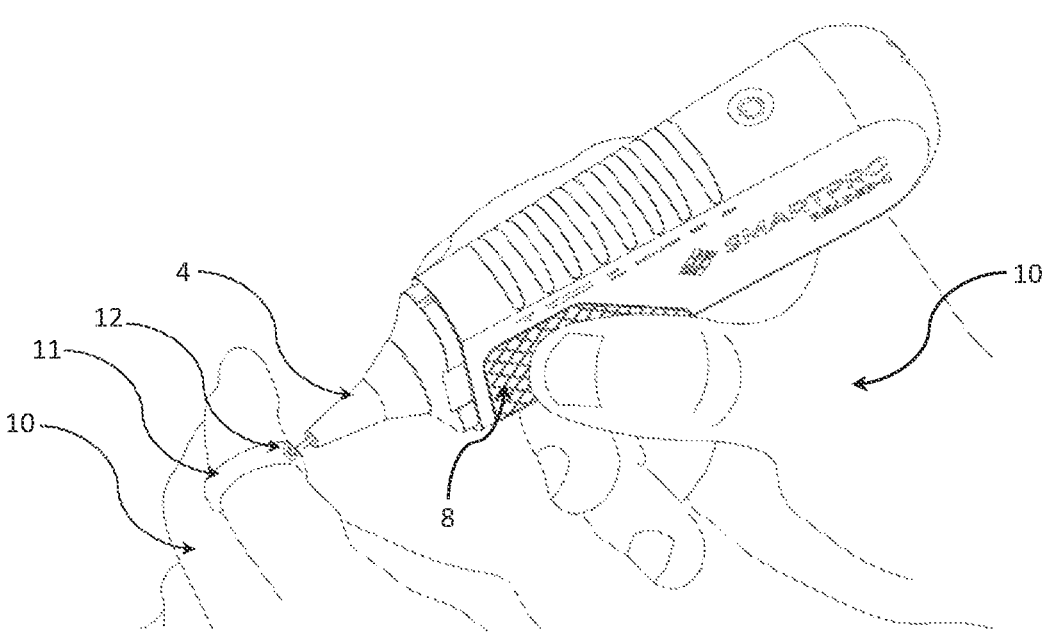
FIG. 1B is a simulation of an actual testing operation of a mounted gemstone, in accordance with an embodiment of the present disclosure.
Figure 1C:
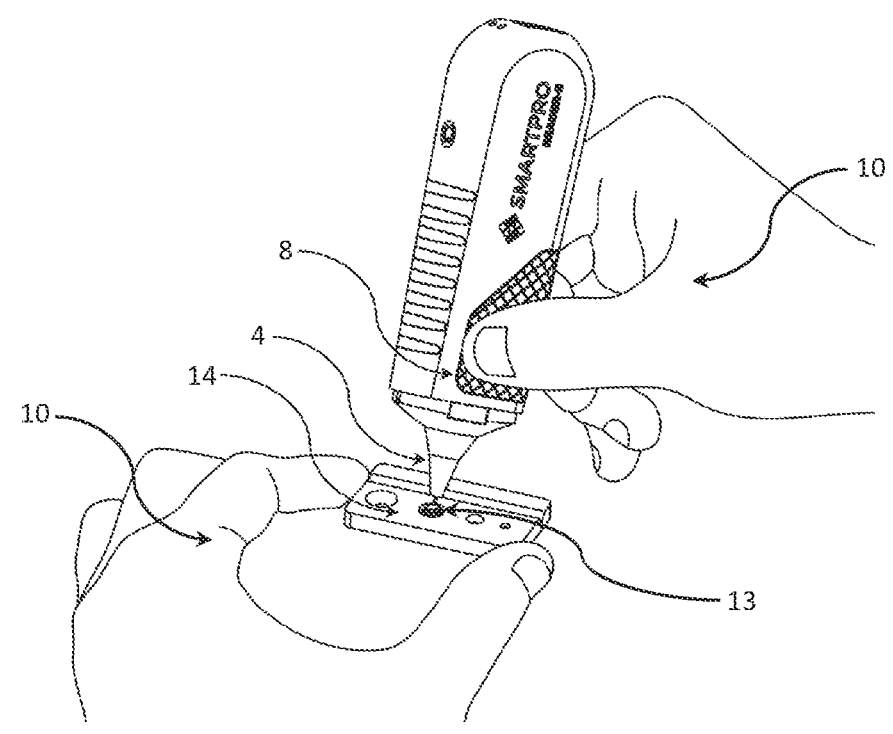
FIG. 1C is a simulation of an actual testing operation of a loose gemstone, in accordance with an embodiment of the present disclosure.

FIG. 1B is a simulation of an actual testing operation of a mounted gemstone 12, in accordance with an embodiment of the present disclosure. The common material used to hold a jewelry stone is a metal 11 which has a high thermal conductivity. In the current embodiment, the metal 11 is a metal ring including the mounted gemstone 12. To detect whether the probe 4 touches the metal 11 or Natural Diamond or Synthetic Diamond which have high thermal conductivity, the apparatus 100 determines whether the probe 4 is in contact of the metal 11 by a closed loop conductivity test with the use of both hands 10 of an operator or tester or user. If the probe 4 touches a conductive material such as the metal 11, the LED indicator 6 is configured to blink repeatedly and the apparatus 100 is configured to provide audio output as "Metal Alert" by way of the speaker 7. FIG. 1C is a simulation of an actual testing operation of a loose gemstone 13, in accordance with an embodiment of the present disclosure. In this embodiment, the loose gemstone 13 may be placed on a slot of a metal tray 14 and the user may hold the apparatus 100 at the conductive grip 8 with one hand 10 and the other hand 10 holding the metal tray 14.

The test specimen (the loose gemstone 13) is held in position and the tester device 100 is positioned in contact with the test specimen. In particular, the probe 4 may be positioned on a flat surface of the test specimen, such as a table facet of the loose gemstone 13. The tester device 100 includes electronic circuitry configured to perform testing and identification of the test specimen. The test specimen thus may be held in position by holding a jewelry in which the mounted stone 12 is mounted or by using a metal or conductive holder (e.g., the metal tray 14) for the loose gemstone 13. The tester device 100 is designed to perform testing both thermal and electrical conductivity on the test specimen. In performing the test, the probe tip 5 of the probe 4 is held in contact with the table facet of the gemstone 12 or 13 and held perpendicular to the table facet.

The probe 4 is to be properly positioned with the gemstone 12 or 13 being tested. In some embodiments, spacing between the probe 4 and the gemstone 12 or 13 or, the probe 4 not being placed within the table facet and in good contact with the gemstone 12 or 13, may lead to inaccurate readings or identifications. In one embodiment, an entire face of the probe 4 must be in full contact with the table facet of the gemstone 12 or 13 or at least a flat surface of the gemstone 12 or 13 to obtain accurate thermal test readings.

Figure 2:
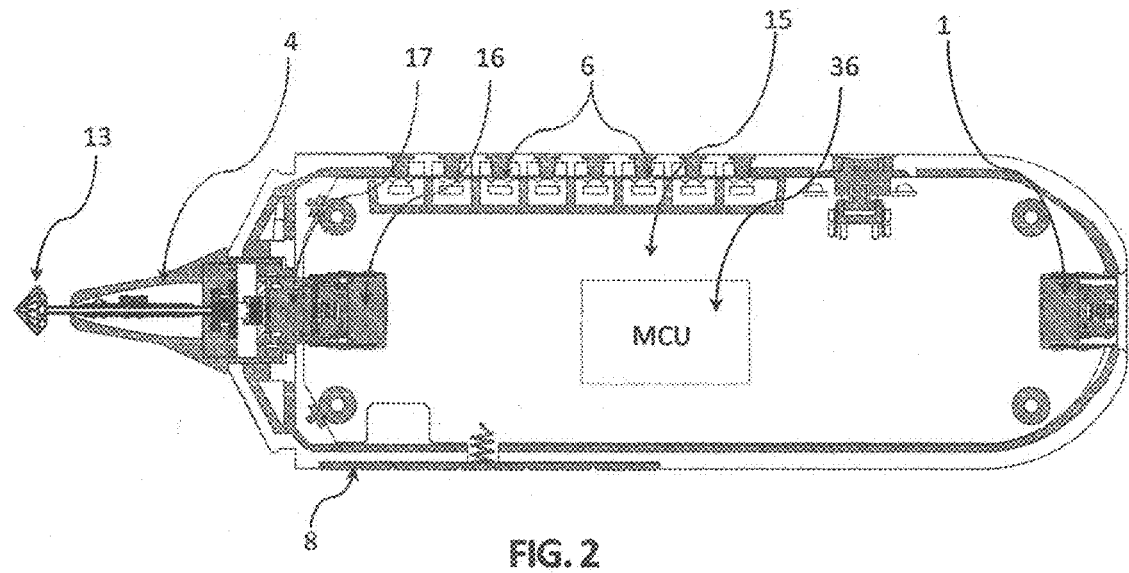
FIG. 2 is a cross-sectional view of the apparatus of FIG. 1A, in accordance with an embodiment of the present disclosure.

FIG. 2 is a cross-sectional view of the apparatus 100, in accordance with an embodiment of the present disclosure. The apparatus 100 includes a housing in which multiple components of the apparatus 100 are disposed. The handheld body 2 (handheld device) includes a standardized connection 16 and the probe 4 includes a complementary standardized connection 17. The probe 4 is removably coupled to the handheld body 2 using the standardized connection 16 and the complementary standardized connection 17. In one embodiment, the standardized connection 16 is a female connection and the complementary standardized connection 17 is male connection. The probe 4 is adapted to be removed from the handheld body 2 without using any external tools. In one example, the standardized connection includes a universal serial bus (USB) connection. A USB-C female socket 16 (standardized connection) is assembled in a printed circuit board (PCB) 15 as the receiver of the replaceable test probe 4 with a USB-C male plug 17 (complementary standardized connection). The USB type C is designed to connect to either side (reversible).

In one embodiment, the input power port 1 for charging the battery of the apparatus 100 is the same type of connector for the replaceable test probe 4 but in the case of mistaken connection, both the apparatus 100 and the replaceable test probe 4 are configured to detect faults and may not be damaged. In one example, the input power port 1 is a USB-C female connector. Utilization of USB connector for the probe 4 makes replacement of the probe 4 easy in case of damage or malfunctions. It will be apparent to a person skilled in the art that in the current embodiment, the standard connection includes the USB connection, however the scope of the present disclosure is not limited to it and in various other embodiments, the standard connection includes any suitable connection, without deviating from the scope of the present disclosure.

The apparatus 100 further includes a microcontroller 36 that is configured to identify a type of the gemstone 12 or 13 under test based on at least one of: the electrical properties, the thermal properties, and the optical properties of the gemstone 12 or 13. The microcontroller 36 presents the identification result to the user or tester by way of the visual indicator 6.

Figure 3:
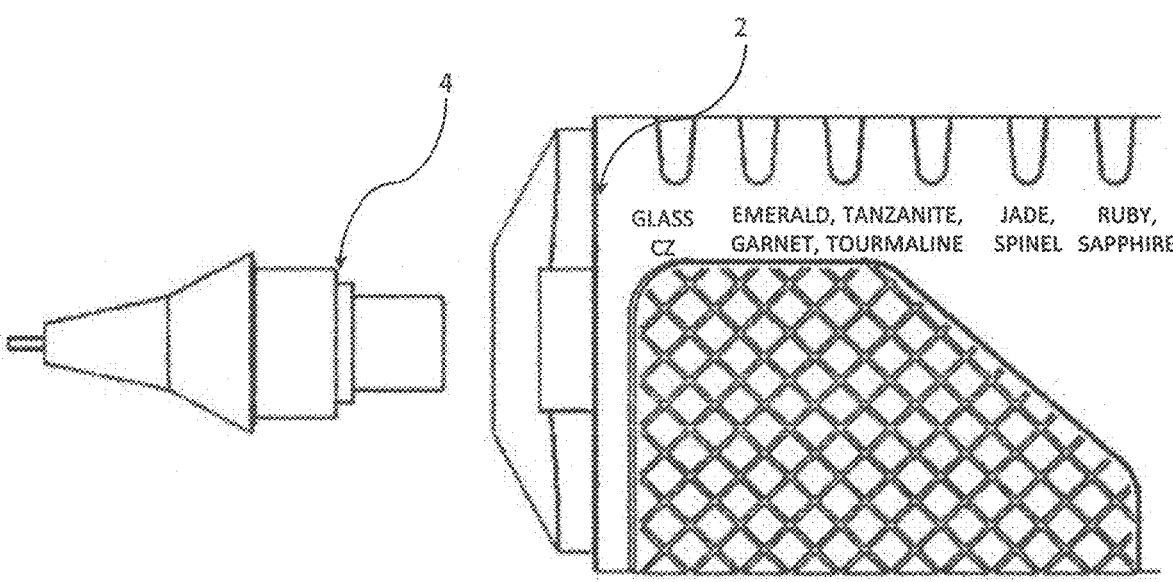
FIG. 3 illustrates a replaceable test probe detached from the apparatus of FIG. 1A, in accordance with an embodiment of the present disclosure.

FIG. 3 illustrates the replaceable test probe 4 detached from the handheld body 2 of the apparatus 100, in accordance with an embodiment of the present disclosure. The probe 4 is prone to damage in long time of usage because of the required contact with the gemstone under test during the initiation of testing. The probe 4 is removable and replaceable. The apparatus 100 is designed to easily replace the test probe 4 by detaching the test probe 4 from the handheld body 2. It will be understood by a person skilled in the art that the probe 4 may be used as a plug-and-play device along with the handheld body 2 and no external tools are required to couple or decouple the probe 4 to or from the handheld body 2.

Figure 4:
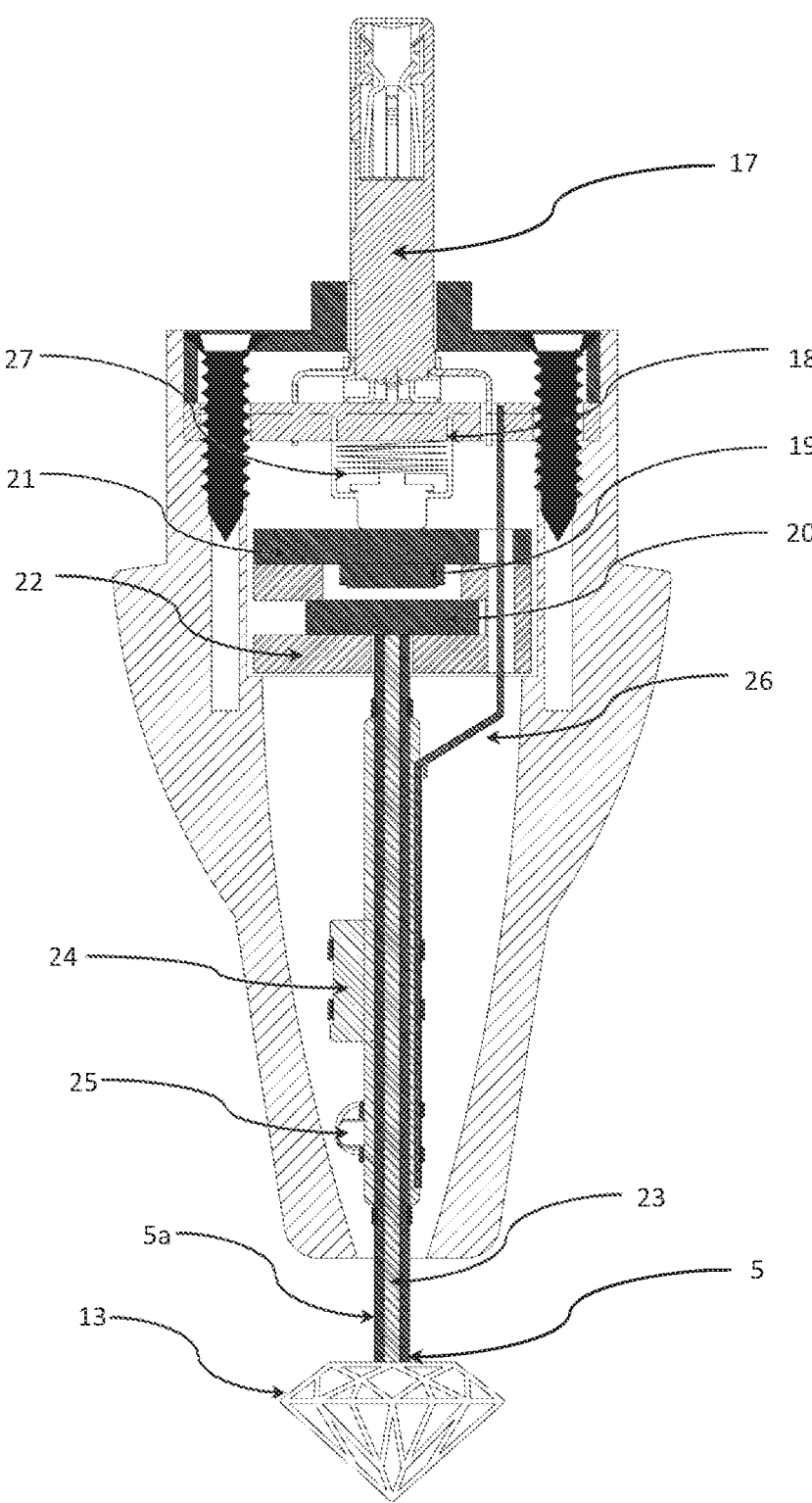
FIG. 4 is a cross sectional view of the replaceable test probe of FIG. 3, in accordance with an embodiment of the present disclosure.
Figure 5:
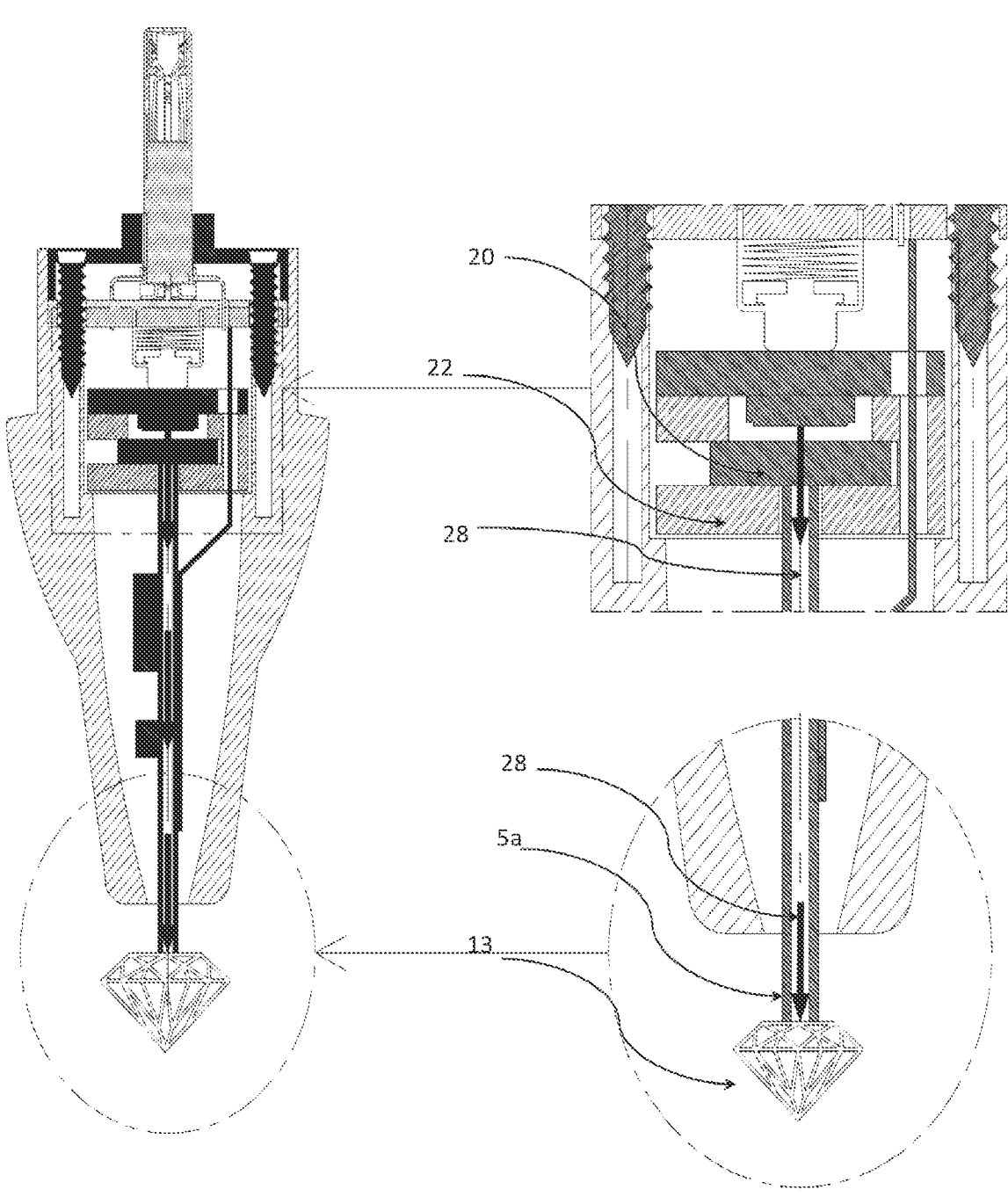
FIG. 5 illustrates an operation of an ultra-violet (UV) light emitting diode (LED) source of the replaceable test probe of FIG. 4, in accordance with an embodiment of the present disclosure.

FIG. 4 is a cross sectional view of the replaceable test probe 4, in accordance with an embodiment of the present disclosure. FIG. 5 illustrates an operation of an ultra-violet (UV) light emitting diode (LED) source 19 of the replaceable test probe of FIG. 4, in accordance with an embodiment of the present disclosure. The probe 4 receives power from the input power source 1 by way of the complementary standardized connection 17. The probe includes a PCB 18 on which the complementary standardized connection 17 is assembled. The probe 4 further includes an optical testing assembly including the UV LED source 19 and an optical window 20. The UV LED source 19 is coupled with a UV LED PCB 21 which is coupled with the PCB 18 to receive power for an operation of the UV LED source 19. The optical window 20 is housed in an optical window housing 22. The UV LED source 19 is configured to generate at least one of a short wavelength UV light and a long wavelength UV light and illuminate the gemstone 13 under test with at least one of the short wavelength UV light and the long wavelength UV light.

The probe 4 further includes a copper tube 5a, at least one optical fiber 23 positioned within the copper tube 5a, and the probe tip 5 that makes contact with a flat surface of the gemstone 13 under test. The copper tube 5a is coupled with a thermal testing assembly including a heating element 24, a thermistor 25, and magnetic wires 26 which are connected to the PCB 18. In one embodiment, the thermistor 25 is a negative temperature coefficient (NTC) thermistor. In one embodiment, the heating element 24 is an surface mount device (SMD) resistor. The heating element 24 may be configured to provide a constant/time-invariant heat output accounting for the fact that the resistance of a heating wire changes with temperature. An inconsistent power output is expected if a constant current is applied. The heating element 24 is configured to provide the heat generated to the copper tube 5a. The thermistor 25 is operably coupled to the copper tube 5a, and configured to sense the temperature of the copper tube 5a. The thermistor 25 may be configured to provide the sensed temperature to the microcontroller 36 by way of the magnetic wires 26. The microcontroller 36 is thus configured to determine an amount of heat transfer from the copper tube 5a to the gemstone 13 under test. If the probe tip 5 is surrounded by air or held in contact with a poor thermal conductor such as a Cubic Zirconia, a temperature of the probe tip 5 remains high. If the probe tip 5 is held in contact with a Moissanite or CVD/HPHT or Earth-mined diamond, the heat energy is conducted away rapidly and the temperature of the copper tube 5a falls. In one method of thermal conductivity testing, the amount of time taken for a predetermined temperature fall is used to test for thermal conductivity. In other methods, for example, a resistance to a rise in temperature may be used.

In some embodiments optical testing begins after thermal testing. The copper tube 5a is assembled perpendicularly with the optical window 20. The UV LED source 19 mounted on the UV LED PCB 21 is positioned perpendicularly with the copper tube 5a with the optical fiber 23. The optical fiber 23 is configured to emit light towards the gemstone 13.

FIG. 5 illustrates the UV light 28 passing through the optical window 20 and the optical fiber 23 to illuminate the gemstone 13. The UV light 28 helps a Moissanite to increase its electrical conductivity by photoconductivity effect, thereby distinguishing the Moissanite from Natural Diamond using UV light and high voltage electrical conductivity test.

The copper tube 5a and the UV LED source 19 are coupled to the PCB 18 by way of the magnetic wires 26. The test probe 4 is supplied power from the PCB 15 of the tester device 100 by way of the standard connection 16 and 17, e.g., the USB-C connectors. In one embodiment, the probe 4 further includes a switch 27 (e.g., a detection switch). The switch 27 is configured to detect a contact between the probe 4 and the stone under test. In one example, the switch 27 is one of an electronic mini-switch (e.g., a mini tact switch) and a pressure sensitive sensor. The force received by the probe tip 5 from a push while contacting the probe tip 5 to the gemstone 13 is relayed to the optical window 20 and the optical window housing 22, further to the UV LED PCB 21, and finally relayed to the switch 27. If the switch 27 detects the push, a signal may be sent to the microcontroller 36 to turn ON the UV LED source 19 and start the testing process.

The UV LED source 19 illuminates the gemstone 12 or 13 with the UV light 28 passing through the optical window 20 and the optical fiber 23.

Figure 6:
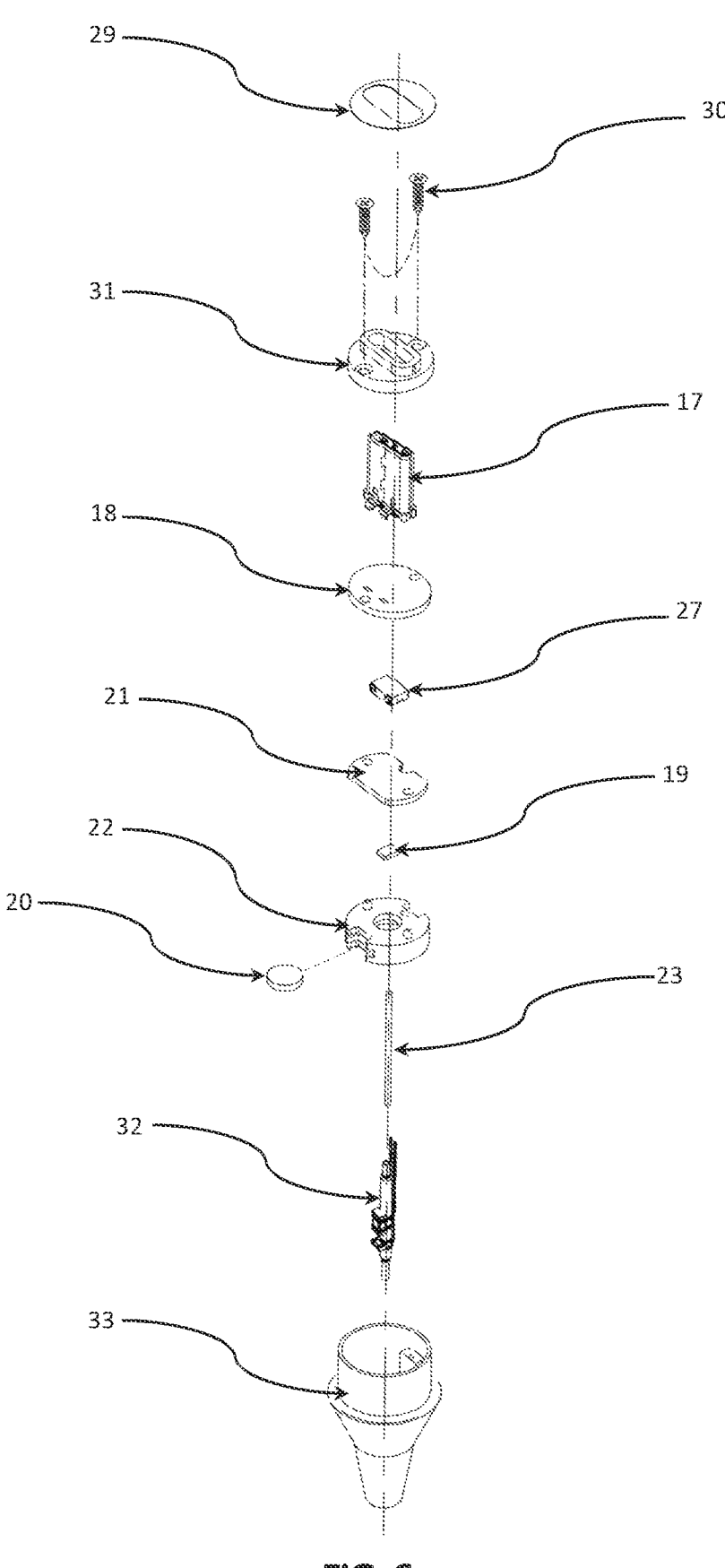
FIG. 6 is an exploded perspective view of the replaceable test probe of FIG. 4, in accordance with an embodiment of the present disclosure.

FIG. 6 is an exploded perspective view of the replaceable test probe 4, in accordance with an embodiment of the present disclosure. FIG. 6 illustrates the exploded perspective view of the replaceable test probe which is composed of the following parts: body parts 31 and 33 to hold and protect inner parts 32, the complementary standardized connector 17, the PCB 18, the UV LED source 19 mounted on the UV LED PCB 21, the optical window 20 housed in the optical window housing 22, the copper tube 5a with the optical fiber 23, the switch 27, body screws 30 and a sticker cover 29 for the body screws 30. The body part 31 has multiple openings to receive the body screws 30 and the body part 33 has multiple holes to receive the body screws 30 to secure the components of the probe 4. In one example, the body parts 31 and 33 are made from plastic.

Figure 7A:
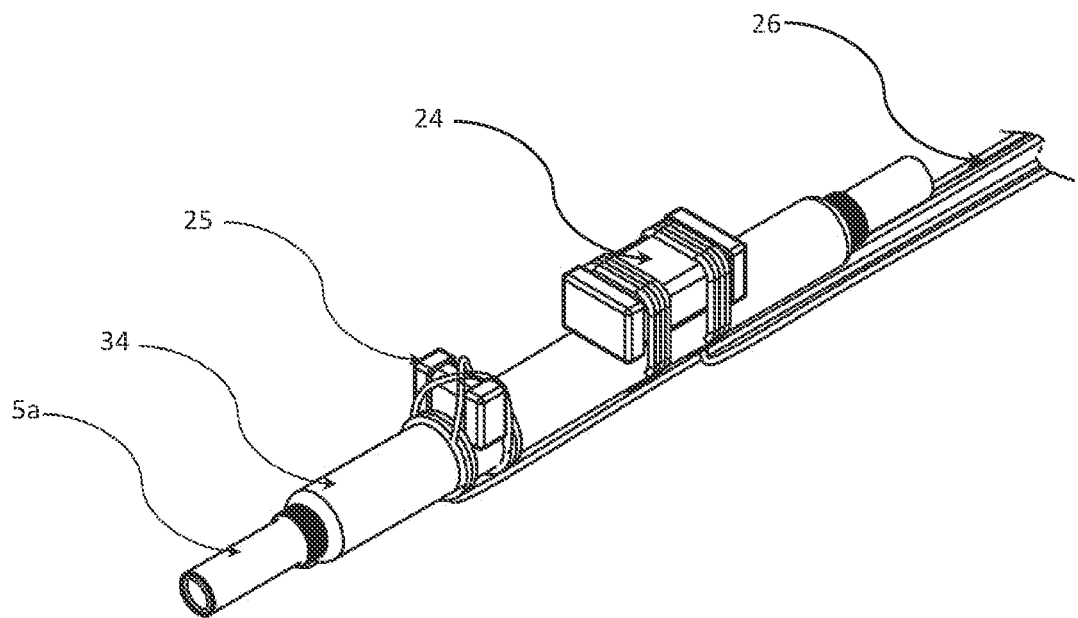
FIG. 7A is an isometric view of a thermal copper tube with a thermistor of the apparatus, in accordance with an embodiment of the present disclosure.
Figure 7B:
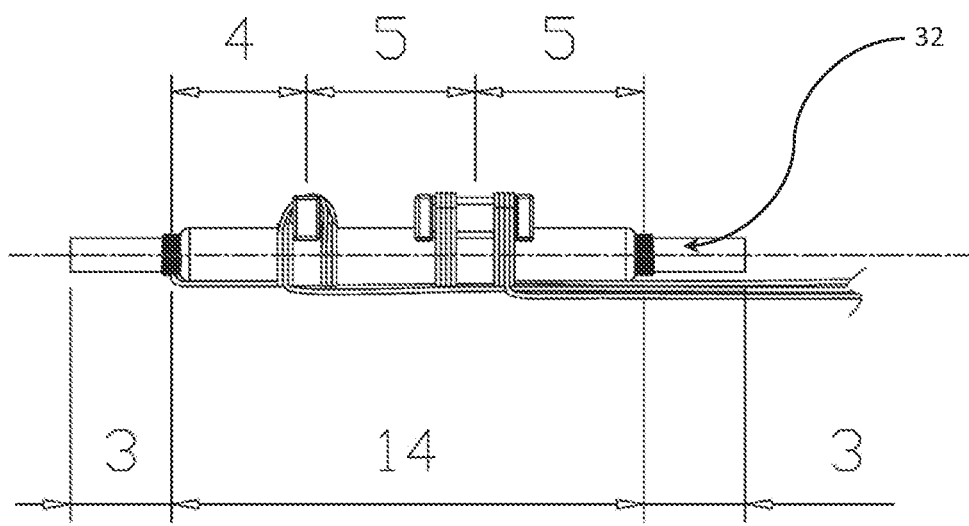
FIG. 7B is an isometric view illustrating dimensions of the thermal copper tube with the thermistor of the apparatus, in accordance with an embodiment of the present disclosure.

FIG. 7A is an isometric view of a thermal copper tube with a thermistor of the apparatus, in accordance with an embodiment of the present disclosure. FIG. 7B is an isometric view illustrating dimensions of the thermal copper tube with the thermistor of the apparatus, in accordance with an embodiment of the present disclosure.

The copper tube 5a is heated during the initiation of the operation of the apparatus 100 (warming-up) and continuously heated during idle and thermal conductivity testing. In some embodiments, the copper tube 5a may be always heated and be ready for testing a gemstone. The heating element 24 and the thermistor 25 are coupled with the copper tube 5a locked by glue and rolled over by the connecting (magnetic) wires 26 to lock in place. In one embodiment, A shrinkable tube 34 is used to isolate the heating element 24 and the thermistor 25 from the copper tube 5a to prevent short circuit. The heating element 24 and the thermistor 25 are coupled with the microcontroller 36 (hereinafter referred to as the microcontroller unit (MCU) 36) to control and monitor the temperature for the stability of the desired temperature. In the thermal conductivity test of the apparatus 100, the stone's temperature is not being measured but rather the level or amount of heat transferred from the copper tube 5a to the gemstone 12 or 13 is being measured and tested. This is by measuring the voltage difference of the two wires of which one is soldered on the copper tube 5a with 4-5 mm distance from the heating element 24 and the other wire is soldered near the thermistor 25 at the opposite side of the copper tube 5a. The measured voltage is amplified by an operational amplifier (OP-AMP) circuit and the amplified output is measured by the MCU 36. The MCU 36 is adapted to wait for a stable reading for 2-3 seconds and obtain the highest stable data for comparing with a threshold value of the gemstone 12 or 13 that are preset by a program associated with the MCU 36.

Figure 7C:
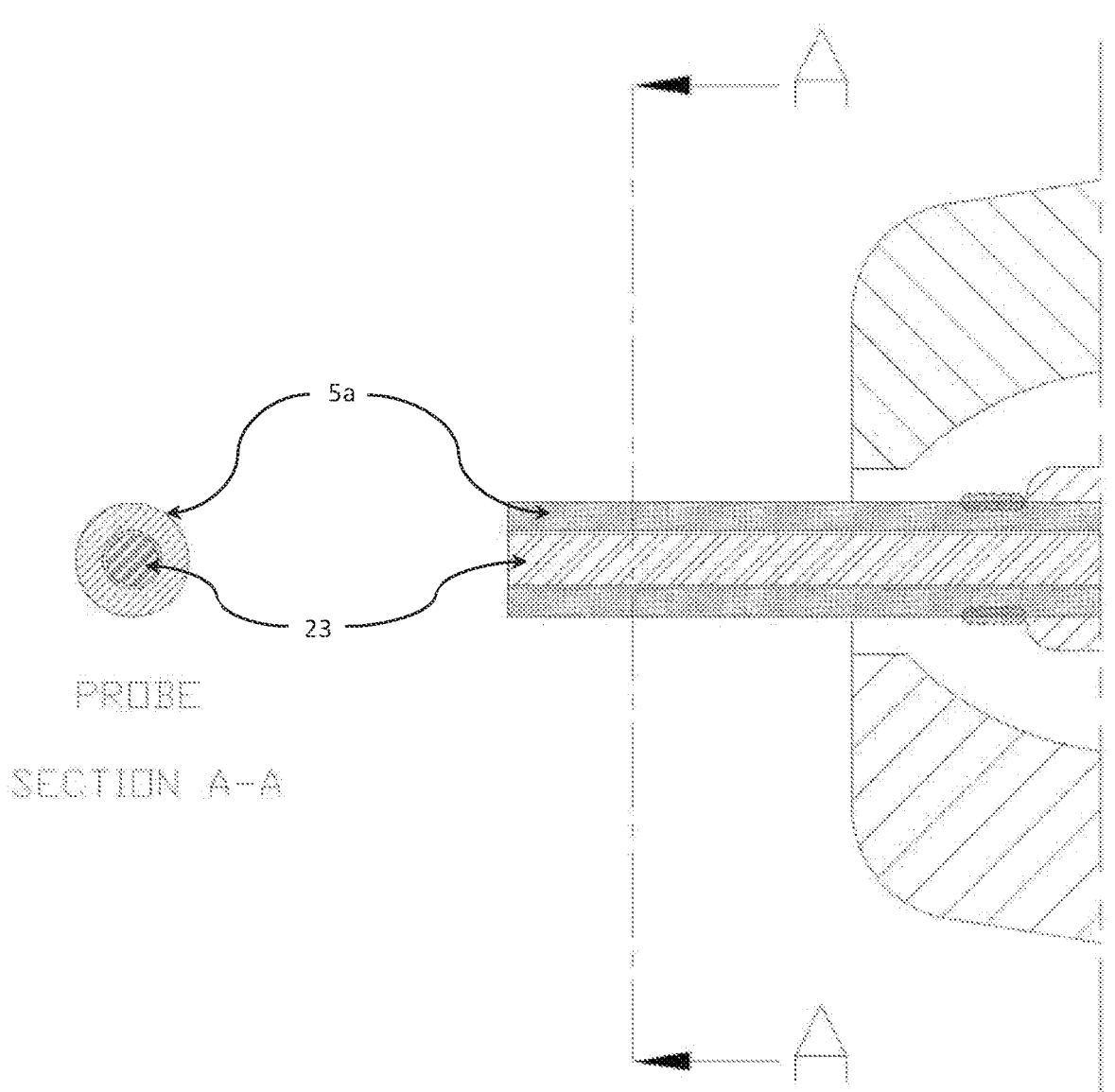
FIG. 7C is a cross sectional view of a probe tip of the thermal copper tube with fiber rod, in accordance with an embodiment of the present disclosure.

FIG. 7C is a cross sectional view of the probe tip 5 of the thermal copper tube with fiber rod, in accordance with an embodiment of the present disclosure. In one example, the copper tube 5a has an outer diameter of 1.0 mm with an inner diameter of 0.5 mm. The optical fiber 23 has a diameter of 0.4 mm.

Figure 8A:
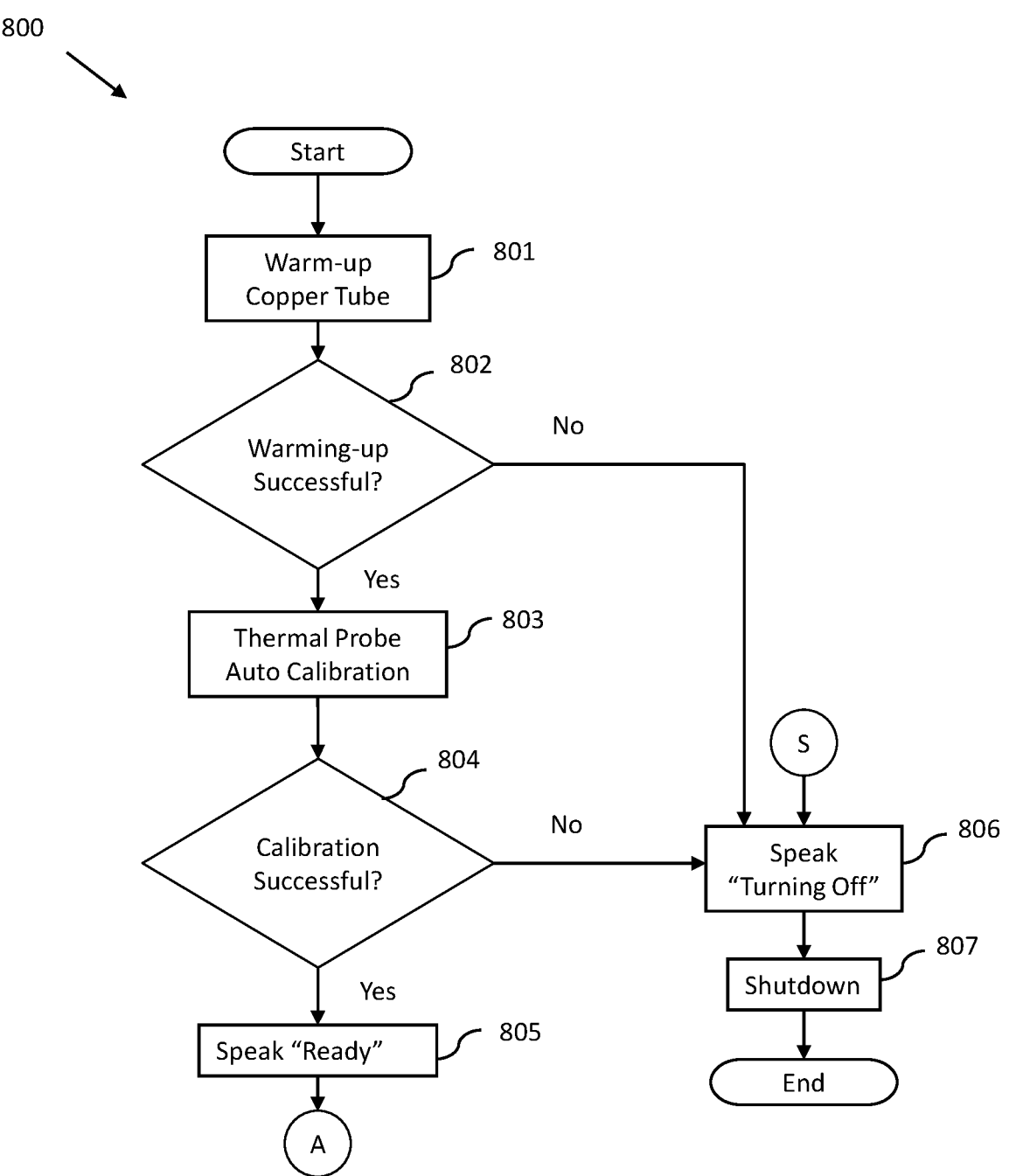
FIGS. 8A-8C, collectively, represent a flow chart illustrating a mode of operation of the apparatus of gemstone testing, in accordance with an embodiment of the present disclosure.
Figure 8B:
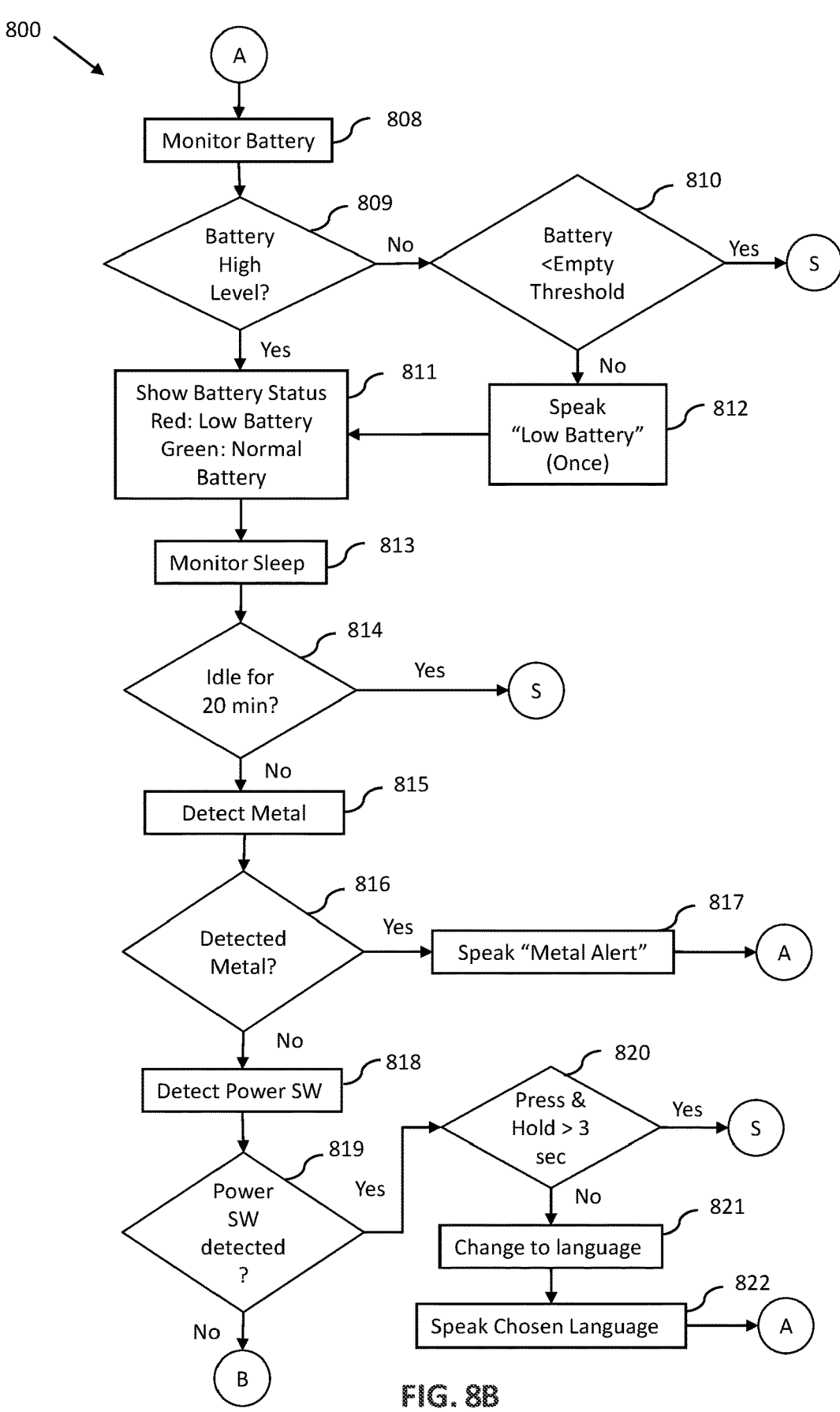
Figure 8C:
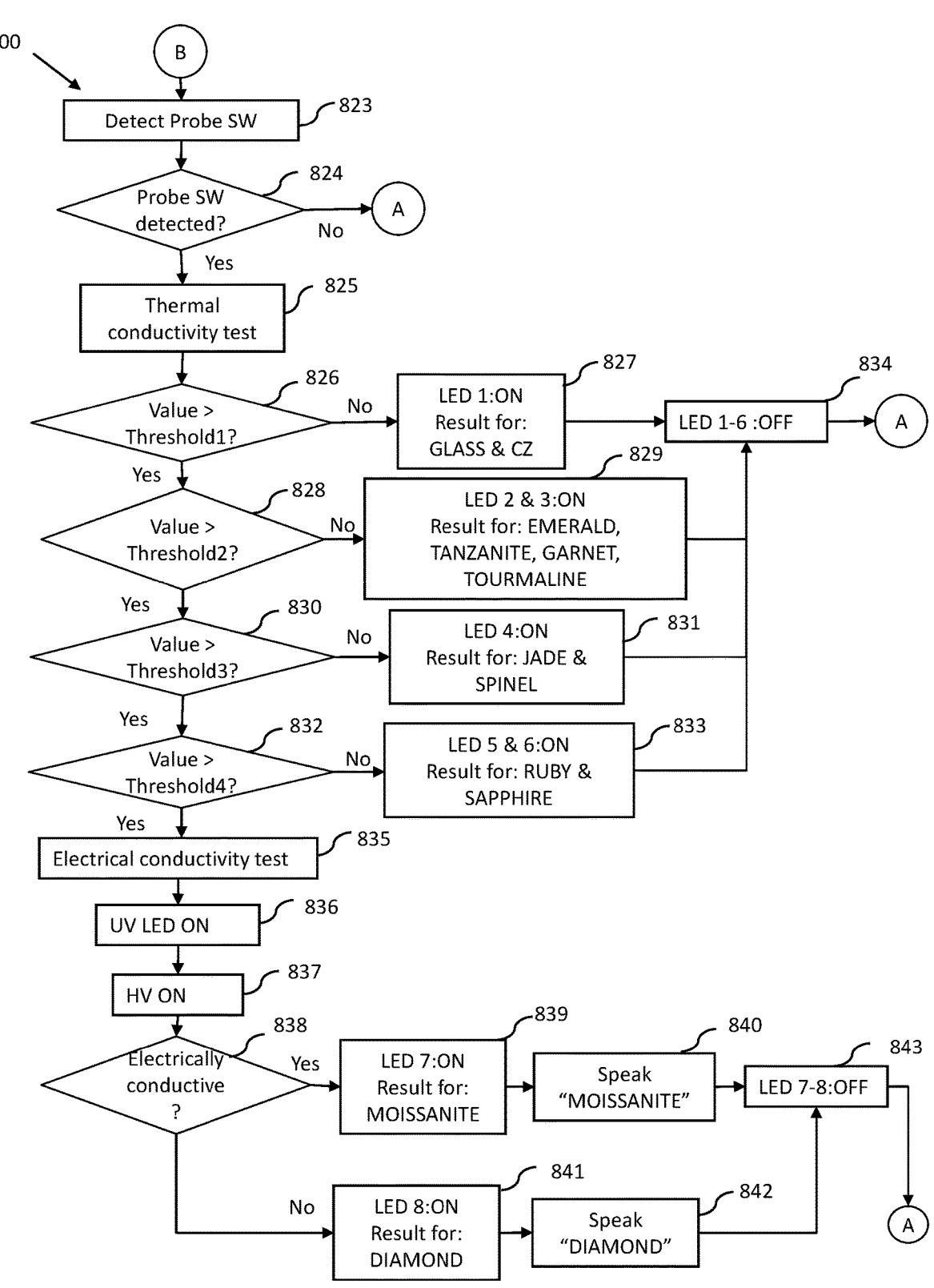

FIGS. 8A-8C, collectively, represent a flow chart 800 illustrating a mode of operation of the apparatus 100 of gemstone testing, in accordance with an embodiment of the present disclosure.

Referring now to FIG. 8A, at 801, the copper tube 5a is warmed-up. Once turned on, the copper tube 5a is heated by the heating element 24 and the temperature of the copper tube 5a is sensed by the thermistor 25 until it reaches the desired temperature for testing. At 802, successful warm-up of the copper tube 5a is determined. After the successful warm-up, at 803, the auto-calibration of the probe 4 is performed. The tester device 100 calibrates itself using stored calibration data which is stored in a memory card such as an SD Card. At 804, successful calibration of the probe 4 is determined. If the calibration is successful, at 805 a ready signal is sent to the speaker 7 to output audio information "Ready" to indicate that the apparatus 100 is ready for testing. The steps 801-805 are initialization steps. If in the case of failure in warming-up or calibration, the apparatus 100 may proceed to shut down (806 and 807). At 806, a turn-off signal is sent to the speaker 7 to output audio information "Turning Off" to indicate that the apparatus 100 is shutting down. At 807, the apparatus 100 shuts down.

Referring now to FIG. 8B which illustrates an initial part of a main loop of the functions which includes the following: Battery Monitoring, Sleep Monitoring, Metal Detection, and Power Switch Detection. At 808, a battery level of the apparatus 100 is monitored. The MCU 36 determines the battery level of the battery and controls two LEDs for battery indicator, Green LED for Normal Battery and Red for Low level battery. At 809, the MCU 36 determines whether the battery level of the battery is high. If the battery level is low, at 810, the MCU 36 determines whether the battery level is less than an empty threshold. If the battery level is less than the empty threshold, the shutdown process is initiated. If the battery level is high, at 811, the battery status is displayed with the two LEDs for the battery indicator, the Green LED for Normal Battery and the Red for Low level battery. If the battery level is not less than the empty threshold, at 812, a low battery signal is sent to the speaker 7 to output audio information "Low Battery" to indicate that the battery level of the apparatus 100 is low (indicated with red LED).

At 813, sleep monitoring is performed. At 814, the MCU 36 determines if the apparatus is idle for 20 minutes. If the apparatus is idle for 20 minutes, the shutdown process is initiated. If the apparatus is not idle for 20 minutes, the metal detection operation is performed.

At 815, the apparatus 100 initiates the metal detection function. At 816, the apparatus 100 determines whether metal is detected. If metal is detected, at 817, a metal alert signal is sent to the speaker 7 to output audio information "Metal Alert" to indicate that the metal is detected by the apparatus 100 and perform step 808 again. Metal detection is important before proceeding on Thermal and Electrical Conductivity Test. Natural Diamond, Synthetic Moissanite and CVD/HPHT synthetic stones have high thermal conductivity similar to metal. The apparatus 100 performs the metal detection test first and does not allow proceeding on to next process if the probe tip 5 touches a metal or conductive material. "Metal Alert" may be heard from speaker with the visual indicator 6 (LED lights) blinking repeatedly to indicate this error alert.

If metal is not detected, at 818, power switch detection function is performed. At 819, activation of the power switch 3 is determined. If the power switch is activated, at 820, the apparatus 100 determines whether the power switch is pressed and held for more than three seconds. If the power switch is pressed and held for three seconds, the shutdown process is initiated. If the power switch is pressed and held for less than three seconds, at 821, an output language of the apparatus 100 is changed. At 822, the selected language is indicated by outputting audio information corresponding to the selected language by way of the speaker 7, and the step 808 is performed again. In some embodiments, multiple languages are made available. In one embodiment, there are 11 available languages saved on the SD card of the apparatus 100. Examples of the language include, but are not limited to, English, Chinese, French, German, Italian, Spanish, Japanese, Thai, Hindi, Korean, and Russian. To change the language, during the idle state of the tester device 100, the power switch 3 pressed once after which the tester device 100 is configured to speak the active language. Press the power switch 3 again to choose another language. The last selected language may be saved on the SD card as the default language setting. In one example, the original default language is English.

Referring now to FIG. 8C which includes the testing and results. The testing starts if there is pressure detected on the sensor probe tip 5 which is activating the switch 27 inside the probe 4 and sends a signal to the MCU 36. At 823, the probe switch detection function is performed. At 824, an activation of the switch 27 is determined. If the switch 27 is not activated step 808 is performed again. If there is a continuous press on probe and detected a non-metal material, e.g., the switch 27 is activated, at 825 a thermal conductivity test is conducted. The thermal conductivity test is done by measuring the amount of heat transferred from the copper tube 5a to the gemstone 12 or 13. A small amount of voltage is being amplified by an OP-AMP circuit and the amplified output is measured by the MCU 36. When the testing starts, the voltage output from the operational amplifier circuit increases and the microcontroller 36 waits for the output to be stable before obtaining a final reading. The final reading is compared to threshold values from 1 to 4. At 826, if the final reading is less than threshold 1, the gemstone result range is within Glass and Cubic Zirconia (CZ), and at 827, an LED 1 of the visual indicator 6 is turned ON. At 828, if the final reading is greater than threshold 1 but less than threshold 2, the result range is within Emerald, Tanzanite, Garnet, and Tourmaline, and at 829, an LED 2 and an LED 3 of the visual indicator 6 are turned ON. At 830, if the final reading is greater than threshold 2 but less than threshold 3, the result range is within Jade and Spinel, and at 831, an LED 4 of the visual indicator 6 is turned ON. At 832, if the final reading is greater than threshold 3 but less than threshold 4, the result range is within Ruby and Sapphire, and at 833, an LED 5 of the visual indicator 6 is turned ON. After 827, 829, 831, and 833, at 834, the LEDs 1-6 are turned OFF and the step 808 is performed again. If the thermal conductivity data (the final reading) is greater than the threshold 4 value, at 835, the electrical conductivity testing is performed with the help of the UV LED source 19 using photoconductivity effect. Photoconductivity is an optical and electrical phenomenon in which a material becomes more electrically conductive due to the absorption of electromagnetic radiation such as visible light, ultraviolet light, infrared light, or gamma radiation.

Moissanite is a naturally occurring silicon carbide and its various crystalline polymorphs. Moissanite has the chemical formula SiC (Silicon carbide), also known as carborundum, is a hard chemical compound containing silicon and carbon. A semiconductor, it occurs in nature as the extremely rare mineral Moissanite. Since Moissanites have different electrical conductivity levels, using a photoconductivity effect by using UV increases its electrical conductivity and it is easier to distinguish Moissanite from Natural Diamonds which are not electrically conductive.

Using a voltage multiplier circuit with an output of 500V to 600V DC (high voltage, low current) along with the illumination of UV on the stone, hard Moissanite especially with low electrical conductivity (transparent color) may be distinguished from Natural Diamond. The MCU 36 controls the voltage multiplier circuit to make a high voltage pulse for about 350 ms. This HV circuit has a high resistance resistor connected on the output side to have a very low current for preventing user from feeling the current flow while having the high voltage for testing. Apparatus is designed to detect for non-metal first before proceeding for Electrical Conductivity test to prevent possible improper testing. At 836, the UV LED source 19 is turned ON, and at 837, the high voltage circuit is turned ON. The test probe 4 is connected to a Schmitt-trigger NAND gate (both inputs are shorted together) and sends signal to the MCU 36 to monitor the changes. If the detected output is low, meaning there was a current flow detected passing through the stone being tested and it is detected as Moissanite. If the output of NAND gate IC detected high, meaning that there was no current flow passing the stone and it is detected as Natural Diamond. At 838, if the stone is electrically conductive, at 839, an LED 7 of the visual indicator is turned ON for Moissanite. At 840, a moissanite signal is sent to the speaker 7 to output audio information "Moissanite" to indicate that Moissanite is detected by the apparatus 100. At 838, if the stone is not electrically conductive, at 841, an LED 8 of the visual indicator is turned ON for Diamond. At 842, a diamond signal is sent to the speaker 7 to output audio information "Diamond" to indicate that Diamond is detected by the apparatus 100. After 840 and 842, at 843, the LEDs 7 and 8 are turned OFF and the step 808 is performed again to test a different stone or the same stone.

Figure 9:
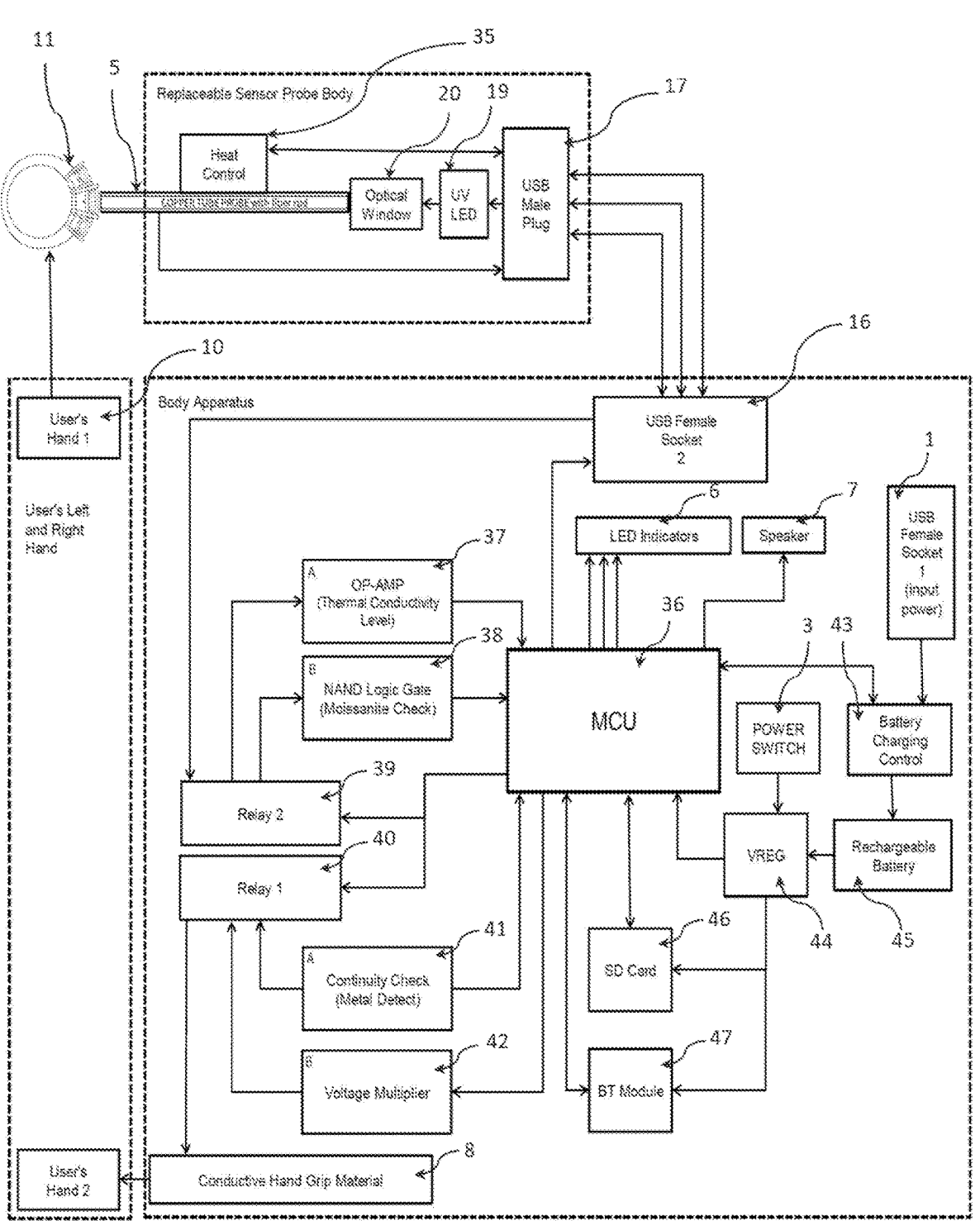
FIG. 9 is a schematic block diagram of the apparatus, in accordance with an embodiment of the present disclosure.

FIG. 9 is a schematic block diagram of the apparatus 100, in accordance with an embodiment of the present disclosure. FIG. 9 depicts a user holding the ring 11 with a mounted stone 12 in one hand 10 and holding at the conductive hand grip material 8 of the apparatus 100 in the other hand 10. The probe 4 (Replaceable sensor probe body) is shown with the probe tip 5 in direct contact with the stone's table facet. In this embodiment, the following parts of the probe 4 are shown in an operable configuration: the probe tip 5 (the copper tube 5a probe with fiber rod), the USB Male Plug 17, the UV LED 19, the optical window 20, and a heat controller 35.

In this embodiment, the following parts of the handheld body 2 (hereinafter also known as body apparatus) are shown in an operable configuration: the power source 1 (USB female socket 1 for input power), the power switch 3, the LED indicators 6, the speaker 7, the conductive hand grip material 8, the USB female socket 16, the MCU 36, an OP-AMP 37, a NAND logic gate 38, relays 39 and 40 (a first relay 40 and a second relay 39), a continuity check circuit 41, a voltage multiplier 42, a battery charging control 43, a voltage regulator (VREG) 44, a rechargeable battery 45, an SD card 46, and a Bluetooth (BT) Module 47.

In operation, the power supply, the rechargeable battery 45 or the power source 1, once turned ON by way of the power switch 3 activates the voltage regulator 44 and the MCU 36. The power source 1 is operably coupled with the battery charging control 43. The battery charging control 43 is configured to receive the power supply from the power source 1, charge the rechargeable battery 45, and monitor a charging level of the rechargeable battery 45. When the charging level of the rechargeable battery 45 is high, the battery charging control 43 discontinues charging of the rechargeable battery 45. The voltage regulator 44 is configured to generate 5V and 3.3V output and provide the generated output to the MCU 36, the SD Card 46, and the BT module 47. The SD Card 46 is configured to store audio files and calibration data, and is operably coupled to the MCU 36 to provide audio files associated with the selected language for indicating the testing and identification results. The BT Module 47 is operably coupled to the MCU 36 and is configured to communicate the testing and identification results to an external electronic device, such as smart phone or tablet, through a wireless communication network, such as Bluetooth. The MCU 36 is configured to control the testing and identification functions of the tester device 100.

The speaker 7 and the LED Indicators 6 are operatively coupled with the MCU 36 and are configured to indicate the testing and identification results to the user audibly and visually. Accordingly, when the test result is generated, a test result signal is generated by the MCU 36 and provided to the speaker 7 to output audio information corresponding to the test result. Further, the MCU 36 turns ON the corresponding LEDs of the LED indicators 6 according to the test result. The MCU 36 comprises a Bluetooth communication unit operably coupled with the BT module 47 to transmit the test result to the BT module 47 which transmits the test result to the external electronic device.

The relays 39 and 40 are shown operably coupled with the MCU 36. The first relay 40 is further coupled with the continuity check circuit 41 which is configured to perform the metal detection function and the voltage multiplier 42 which is configured to perform the electrical conductivity test. The continuity check circuit 41 and the voltage multiplier circuit 42 are coupled with the conductive hand grip material 8 by way of the first relay 40. The second relay 39 is coupled with the OP-AMP 37 which is configured to check the thermal conductivity level and the NAND Logic Gate 38 which is configured to check the electrical conductivity of a gemstone. The OP-AMP 37 and the continuity check circuit 41 are operational at the same time for the metal check function and thermal conductivity check. When the apparatus 100 is required to distinguish Diamond from Moissanite by performing the electrical conductivity test by utilizing the voltage multiplier 42 and the NAND Logic Gate 38, the OP-AMP 37 and the continuity check circuit 41 are operational are inactive.

The copper tube 5a with the optical fiber 23 is operably coupled with the heat controller 35 and the optical window 20. The UV LED source 19 is operably coupled to the USB-C male plug 17 to receive the power supply and emit light towards the optical window 20 and the optical fiber 23. The USB-C male plug 17 and the USB-C female socket 16 are operably coupled with each other for operation of the apparatus 100.

FIG. 8 describes the flow of an example of an operation sequence of the gemstone testing device (the apparatus 100). Once the power switch 3 is powered ON, the tester device 100, using the MCU 36, self-calibrates through a software program. If the tester device 100 is successfully calibrated, "Ready" audio is output from the speaker 7. The sequence and flow of events of FIG. 8A, 8B, and 8C follow. The thermal testing assembly coupled to the copper tube 5a, is configured to provide heat to the copper tube 5a and sense the temperature of the copper tube 5a. The optical testing assembly is configured to generate at least one of the short wavelength UV light and the long wavelength UV light and illuminate the stone under test with at least one of the short wavelength UV light and the long wavelength UV light. The MCU 36 is operably coupled to the thermal testing assembly and the optical testing assembly and configured to determine the amount of heat transfer from the copper tube 5a to the stone under test. The MCU 36 determines at least one of: electrical properties, thermal properties, and optical properties of the stone under test based on at least one of the amount of heat transfer and electrical conductivity. Based on the determined at least one of: the electrical properties, the thermal properties, and the optical properties, the MCU 36 identifies a type of the stone under test. The visual indicator 6 operably coupled to the MCU 36 and configured to indicate the type of the stone under test. In one embodiment, the stone under test is one of an earth-mined diamond, a Type IIa HPHT diamond, a Type IIa CVD diamond, a Simulant, and a Moissanite. The type of the stone under test is one of glass or cubic zirconia, or one of emerald, tanzanite, garnet, and tourmaline, or one of jade and spinel, or one of ruby and sapphire.

A simple thermal conductivity test is incapable of separating Natural Diamond and Synthetic Moissanite from metal because these stones have high thermal conductivity. To separate high thermal conductivity stones from metal using a simple method, a low voltage electrical conductivity test is performed. In one embodiment, the MCU 36 is configured to determine at least two of: the thermal properties, the optical properties, and the electrical properties of the stone under test simultaneously.

Figure 10:
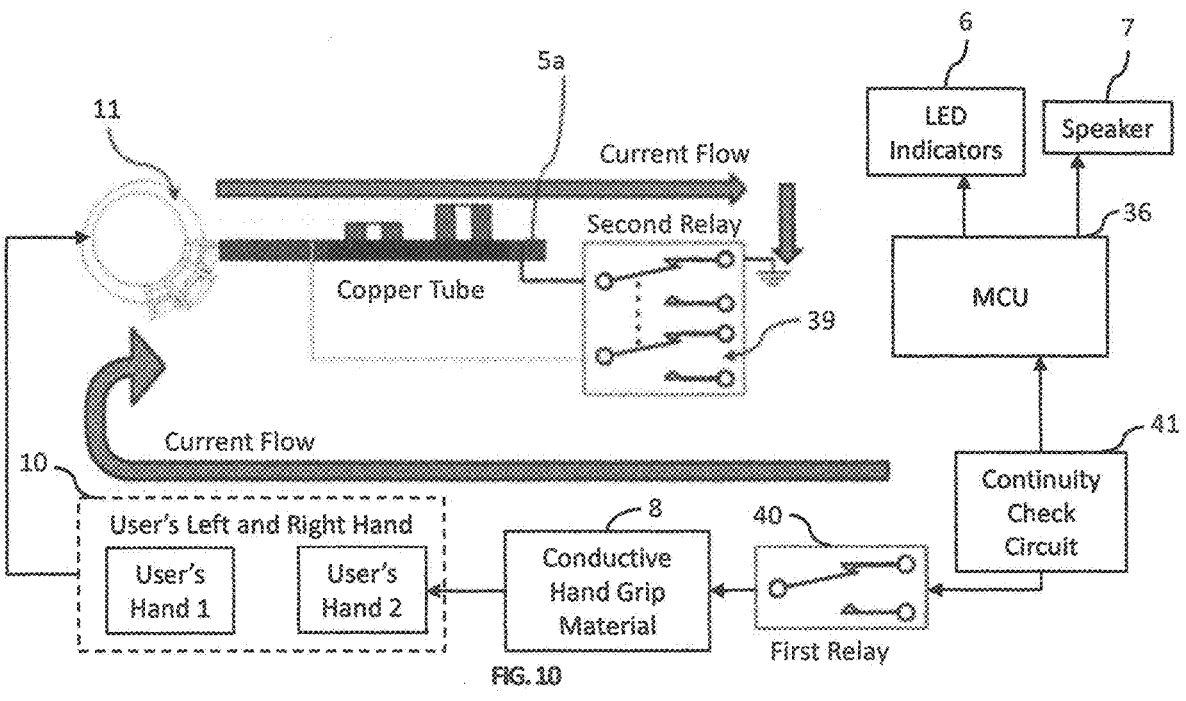
FIG. 10 is a schematic block diagram of the apparatus for metal detection, in accordance with an embodiment of the present disclosure.

FIG. 10 is a schematic block diagram of the apparatus 100 for metal detection, in accordance with an embodiment of the present disclosure. The continuity test includes detecting if there is a closed loop circuit between these following parts and objects of a continuity test assembly: a continuity check (metal detect) circuit 41, the first relay 40, the conductive hand grip material 8, user's two hands (use one hand to hold the apparatus 100 and the other hand to hold stone holder) 10, a conductive stone holder (for mounted setting) 11 or conductive stone tray (for loose settings) 14, the specimen under test, the copper tube 5a, and the second relay 39 to circuit ground. The continuity check circuit 41 has a pull-up resistor (not shown) and the tip 5 of the test probe 4 is connected to circuit ground, this makes a closed-loop circuit if the probe 4 touches a conductive material like the metal 11. In one embodiment, the first and second relays 39 and 40 are double pole double throw (DPDT) relays.

As illustrated in FIG. 10, the copper tube 5a has contact with the prong of the ring 11 which is a conductive material, thus making a closed loop circuit. The continuity check circuit 41 is connected to the MCU 36 for detecting changes in output. If the MCU 36 detects a low voltage amplitude (closed-loop circuit), metal is detected and indicated with the LED indicators 6 blinking and an alarm audio from the speaker 7. If the MCU 36 detects a high voltage amplitude (open-loop circuit), non-metal is detected, and the apparatus 100 may proceed on further testing such as thermal conductivity and high voltage electrical conductivity test.

FIG. 11A is a schematic block diagram of the apparatus for testing thermal conductivity, in accordance with an embodiment of the present disclosure. FIG. 11A illustrates the heat transfer from the copper tube 5a to a stone and the thermal testing assembly coupling: the cooper tube 5a, the second relay 39, the OP-AMP 37, and the MCU 36. The copper tube 5a is coupled with the second relay 39 where the OP-AMP 37 is coupled. The MCU 36 measures the voltage output of the OP-AMP 37 to determine the amount of heat transfer and controls the LED indicators 6 and the speaker 7 for indicating the test results.

FIG. 11B is a schematic block diagram of the apparatus 100 for electrical testing, in accordance with an embodiment of the present disclosure. FIG. 11B illustrates the coupling of the copper tube 5a along with the heating element 24 and the thermistor 25 to the OP-AMP 37, electronic components, and the MCU 36. The heat controller 35 includes the heating element 24 and the thermistor 25, which are responsible for heating the copper tube 5a. The MCU 36 controls a transistor T having an emitter pin coupled to circuit ground and a collector pin coupled to a heating element 24 which is a heating resistor having a pin coupled to the power supply. The temperature of the copper tube 5*a* is monitored by the thermistor 25. The thermistor 25 is coupled to a pull-up resistor R and the circuit ground. The MCU 36 senses a voltage of the thermistor 25. The MCU 36 controls the heating element by changing a duty cycle of Pulse Width Modulation PWM's output depending on the sensed voltage of the thermistor 25 to maintain the desired temperature for testing. By changing the PWM output, the amount of heat emitted by the heating element is controlled. The copper probe 5*a* must be in contact with the stone from the start of the testing until obtaining the result.

FIG. 12 is a schematic block diagram of the apparatus 100 for high voltage electrical conductivity test, in accordance with an embodiment of the present disclosure. Moissanite is electrically conductive while the Natural Diamond is not electrically conductive. Using the high voltage electrical conductivity test, Moissanite and Diamond may be distinguished. The MCU 36 controls the voltage multiplier 42 to output a high voltage value of about 500 to 600V DC. The high voltage pulse time duration is about 350 ms. The high voltage output has a resistor R1 with high resistance to reduce an amount of current flow through other elements of the apparatus 100. If the stone being tested is electrically conductive or a Moissanite stone, a flow of current passes through the following parts and objects: the high resistance resistor R1, the first relay 40, the conductive hand grip material 8, the user's hands 10, the ring's conductive parts 11, Moissanite stone, the copper tube 5*a*, the second relay 39, and a high resistance resistor R2. The UV LED source 19 is turned ON during the high voltage electrical conductivity test to make the stone more electrically conductive by photoconductivity effect. The NAND logic gate 38 has two inputs that are shorted together, and an output coupled to the MCU 36 to monitor the voltage at the high resistance resistor R2. If there is a voltage present at high resistance resistor R2, the output of NAND logic gate 38 is Low and the MCU 36 turns OFF the voltage multiplier 42. The MCU 36 further controls the LED indicator 6 for indicating Moissanite and sends signal to speaker 7 for "Moissanite" audio output. If the stone is not electrically conductive like Natural Diamond, there may be no voltage at high resistance resistor R2, no current flow through the stone, the output of NAND logic gate 38 is high and the MCU 36 further controls the LED indicator 6 for indicating Diamond and sends signal to speaker 7 for "Diamond" audio output.

FIG. 13A illustrates an apparatus 1300 (hereinafter also referred to as "the tester device 1300") for testing and identifying gemstones, in accordance with another embodiment of the present disclosure. The tester device 1300 is powered by the rechargeable battery or the power source 1, for example, a universal serial bus (USB)-C input power. In one embodiment, the tester device 1300 includes a handheld casing 2*a*, the power switch 3 with status indicator, a test probe 4*a* (hereinafter also referred to as "the probe 4*a*") having the probe tip 5, a visual indicator 6*a*, the speaker 7, the conductive hand grip material 8, and the protective cover 9. In one embodiment, the tester device 1300 includes open slots for the speaker 7. In this embodiment, the visual indicator 6*a* is a touch screen display panel 6*a*, for example, a liquid crystal display (LCD). The user may operate the apparatus 1300 by interacting (for example, touch input) with functions on touch screen display panel 6*a*. An identification result may be displayed on the touch screen display panel 6*a*. The touch screen display panel 6*a* is further configured to render for selection a display screen language from several languages. In the embodiment, the probe 4*a* is fixed to the handheld casing 2*a*.

FIG. 13B is a simulation of an actual testing operation of the mounted gemstone 12, in accordance with another embodiment of the present disclosure. The common material used to hold a jewelry stone is a metal 11 which has a high thermal conductivity. In the current embodiment, the metal 11 is a metal ring including the mounted gemstone 12. To detect whether the probe 4*a* touches the metal 11 or Natural Diamond or Synthetic Diamond which have high thermal conductivity, the apparatus 1300 determines whether the probe 4*a* is in contact of the metal 11 by a closed loop conductivity test with the use of both hands 10 of an operator or tester or user. If the probe 4*a* touches a conductive material such as the metal 11, the touch screen display panel 6*a* is configured to display "Metal Alert" and the apparatus 1300 is configured to provide audio output as "Metal Alert" by way of the speaker 7. The apparatus 1300 may perform testing of the loose gemstone 13 in a similar manner.

The probe 4*a* is to be properly positioned with the gemstone 12 or 13 being tested. In some embodiments, spacing between the probe 4 and the gemstone 12 or 13 or, the probe 4*a* not being placed within the table facet and in good contact with the gemstone 12 or 13, may lead to inaccurate readings or identifications. In one embodiment, an entire face of the probe 4*a* must be in full contact with the table facet of the gemstone 12 or 13 or at least a flat surface of the gemstone 12 or 13 to obtain accurate thermal and optical test readings. In the current embodiment shown, the probe 4*a* is not removable and replaceable and is fixed to the handheld casing 2*a*.

FIG. 14A illustrates a partially exploded view of the apparatus 1300, in accordance with another embodiment of the present disclosure. The apparatus 1300 includes a PCB 48 with assembled electronics components including the MCU 36, a metal detector contact spring 49, the copper tube 5*a*, the thermistor 25, the heating element 24, the optical fiber 23, and an optical detector housing 50. The optical detector housing 50 includes an optical window 51 and an optical detector 52. The thermistor 25 and the heating element 24 are coupled with the copper tube 5*a* surrounding the copper tube 5*a*. The optical fiber 23 is positioned within the copper tube 5*a*. The copper tube 5*a* is assembled into an optical fiber bundle head 53. The apparatus 1300 further includes optical fiber bundle legs 54 that are assembled into a housing 55. The housing 55 includes the optical fiber bundle legs 54, UV LEDs 56, an optical lens 57 with an optical lens holder 58. The UV LEDs 56 are 2-in-1 containing the short-wave ultraviolet lights (SWUV) and long-wave ultraviolet lights (LWUV). The apparatus 1300 further includes an optical fiber bundle 59 coupled between the optical fiber bundle head 53 and the optical fiber bundle legs 54. The optical fiber bundle 59 includes multiple optical fibers.

In one embodiment, the apparatus 1300 further includes a force sensor 60 that is disposed within a force sensor housing 61, a silicone rubber 62, and a silicone plastic base 63. The optical detector 52 is mounted on an optical detector PCB 64. The optical detector housing 50 is coupled with the silicone plastic base 63 and the force sensor housing 61 is positioned behind the optical detector 52, such that the silicone rubber 62 is positioned between the force sensor housing 61 and the silicone plastic base 63. In the embodiment, the force sensor 60 is configured to detect a contact between the probe 4*a* and the stone under test. The force received by the probe tip 5 from a push while contacting the probe tip 5 to the gemstone 13 is relayed to the optical detector housing 50, further to the optical detector PCB 64 and the silicone plastic base 63, and finally relayed to the force sensor 60 by way of the silicone rubber 62. If the force sensor 60 detects force from the push, a signal may be sent to the microcontroller 36 to start the testing process. Thus, an activation of the force sensor 60 triggers the testing process.

FIG. 14B illustrates a partial sectional view of the apparatus 1300, in accordance with another embodiment of the present disclosure. The copper tube 5a is surrounded by the optical fiber bundle head 53. The test probe 4a is exposed from exiting the housing to the tip 5 that contacts the table facet of the gemstone 13. The distal end of the copper tube 5a is disposed within the optical detector housing 50 and is coupled to the optical window 51. The optical detector 52 is positioned behind the optical window 51. The force sensor housing 61 is positioned behind the optical detector housing 50. The silicone rubber 62 is coupled between the force sensor housing 61 and the optical detector housing 50. FIG. 14B illustrates the various optical components arranged within the handheld casing 2a, including the optical fibers from the optical fiber bundle 59 separated into two groups. The two groups of the optical fiber bundle 59 are positioned within the housing 55 and the optical lens holder 58 with the optical components for signal coupling between the UV LEDs 56 and the optical fibers. In one example, the UV LEDs 56 are arranged or grouped in a concentric or circular fashion.

FIG. 14C illustrates an operation of the apparatus 1300 for thermal and optical testing, in accordance with another embodiment of the present disclosure. For thermal testing, the heating element 24 and the thermistor 25 are mounted onto the test probe 4a. In one embodiment, the heating element 24 is an SMD resistor. The heating element 24 may be configured to provide a constant/time-invariant heat output accounting for the fact that the resistance of the heating wire changes with temperature. An inconsistent power output is expected if a constant current is applied. The amount of heat transfer from the copper tube 5a to the specimen stone under test is detected by the electronic circuits. If the probe tip 5 is surrounded by air or held in contact with a poor thermal conductor such as a Cubic Zirconia, the temperature of the probe tip 5 remains high. If the probe tip 5 is held in contact with a Moissanite or CVD/HPHT or Earth-mined diamond, the heat energy is conducted away rapidly and the temperature of the copper tube 5a falls. In one method of thermal conductivity testing, an amount of time taken for the temperature to fall to a predetermined value is used to test for thermal conductivity. In other methods, for example, an amount of resistance to a rise in temperature may be used to test for thermal conductivity.

In some embodiments the optical testing begins after the thermal testing. For optical testing, a first light is emitted from the UV LEDs 56 that are configured to emit long and short wavelength light when current flows through the UV LEDs 56. The optical lens 57 is configured to couple the light, e.g., the UV radiation, from UV LEDs 56 into each optical fiber bundle leg 54. In one embodiment, the optical lens 57 is a ball lens. The choice of the ball lens (optical lens 57) is dependent on the Numerical Aperture (NA) of the optical fiber and a diameter of the input source which is a UV LED light beam 56a. The diameter of the UV LED light beam 56a is used to determine the NA of the ball lens. The NA of the ball lens may be less than or equal to the NA of the fiber optic to couple all the light emitted from the UV LEDs 56. The ball lens is positioned at back focal length from the optical fiber.

The ball lenses are associated with a set of parameters such as a diameter of input source (d), a diameter of ball lens (D), an effective focal length of the ball lens (EFL), a back focal length of the ball lens (BFL), and an index of refraction of the ball lens (n).

The EFL is measured from a center of the ball lens by using the equation given below:

$$EFL = nD/(4(n-1))$$

The BFL may be calculated based on the EFL and the D by using the equation given below:

$$BFL = EFL - D/2$$

The numerical aperture (NA) is dependent of the focal length of the ball and may be determined using the below equation:

$$NA = 2d(n-1)/nD$$

The ball lens allows light to travel between the source (the UV LEDs 56) and the optical fibers with minimal losses. When the light travels to the optical fiber bundle head 53, the light is emitted and illuminates the gemstone under test. An amount of optical transmission and absorption of the incident ray depends on the gemstone under test. The tester device 1300 is configured to utilize light reflection methods that may perform optical testing of many different gemstones and gemstones on various types of jewelry. When the tip 5 of the test probe 4a is placed on the table facet of gemstone 13, the UV LED light beam 56a is emitted from optical fiber bundle head 53 and passes into the gemstone 13. In the gemstone 13, there may be an internal reflection back from the cut of the gemstone 13 as shown in FIG. 14D and a reflected light 56b is emitted out from the diamond. The reflected light 56b travels through the optical fiber 23 inside the test probe 4a and passes onto the optical detector 52. In one embodiment, the optical detector 52 is a SiC-photodiode with extended wavelength range for optical measurements in the UV-range. The optical detector 52 is located to receive the reflected light 56b received from the end of test probe 4a and is configured to convert photons (or light) into electrical current. The optical detector 52 provides the electrical current to the microcontroller 36 based on which the microcontroller 36 is configured to determine optical properties of the gemstone under test.

FIG. 14D illustrates critical angles of a diamond, in accordance with an embodiment of the present disclosure. FIG. 14D shows the total internal reflection of Ray 1, which meets the pavilion facets of a diamond at an angle greater than a critical angle θc. Ray 2 meets the pavilion facets at an angle less than the critical angle θc and is refracted out of the pavilion facets. Light rays are reflected back from a gemstone facet at angles to the normal which are greater than the critical angle θc and are refracted out of the gemstone at angles less than the critical angle θc. For a transparent faceted gemstone is to have a bright and sparkling appearance, it is important that as many of the rays as possible entering the gem through its crown facets are reflected from the pavilion facets, and re-emerge from the stone as a result of total internal reflection. To achieve this condition, the lapidary or diamond polisher must adjust the angles of the crown and pavilion facets so that the majority of rays entering the crown facets meet the interior faces of the pavilion facets at angles to the normal which are greater than the critical angle of the stone. If the angles are incorrect, the rays may pass out through the pavilion facets, and the stone may appear dark. It is also important that the rays reflected back from the pavilion facets meet the crown facets at angles less than the critical angle θc. If the rays fail to do this, the rays may be reflected back into the stone again. The critical angle of reflection of a gemstone is dependent on both the Refractive Index (RI) of the gemstone and that of the surrounding medium, as shown in the following equation:

Sine of critical angle=(RI of surrounding medium)/
(RI of gemstone)

If the surrounding medium is air:

Sine of critical angle=1/(RI of gemstone)

Critical angle=Arc sine 1/(RI of gemstone)

To determine the critical angle θc of a gemstone in air, a RI value of the gemstone is simply inverted (e.g., divided from 1.0), and this value is taken as the sine of the critical angle. The angle may be derived from a set of trigonometric tables.

For diamond, with an RI of 2.417,

Sine of critical angle=1/2.417=0.413

Critical angle=Arc sine 0.413=24.43°

Thus, for maximum brilliance, the critical angle is important. In FIG. 14D, a single Ray1 is shown undergoing total internal reflection in a diamond (in either direction). A second Ray2 is shown entering the diamond's table facet at a shallow angle and being refracted out through the back of the stone via the 'cone' formed by the critical angle. Thus, showing the importance of the critical angle in the design of a gemstone's profile.

FIG. 15A and FIG. 15B illustrate perspective views of an architecture of the testing assembly of the apparatus 1300, in accordance with another embodiment of the present disclosure. In FIGS. 15A and 15B, the test probe 4a that is configured to perform both thermal and optical testing, is shown with a metal tube, e.g., the copper tube 5a, which is made from copper in some embodiments. It will be apparent to a person skilled in the art that although in the current embodiment, the metal tube is made of copper, in various other embodiment, various types of metals may be used for the metal tube, preferably metals with high thermal conductivity, without deviating from the scope of the present disclosure. The copper tube 5a has a heater in the form of the heating element 24 mounted on the copper tube 5a, the thermistor 25, and the optical fiber rod 23 inserted internally into the copper tube 5a. The test probe 4a is assembled into the optical fiber bundle head 53 concentrically surrounded by the optical fiber bundle 59 that is divided into two groups. Each group of the optical fiber bundle 59 is coupled with the respective optical fiber bundle leg 54.

FIG. 16A and FIG. 16B are cross sectional views of the optical fiber bundle head 53 with the optical fiber bundle 59 surrounding the copper tube 5a and the internal optical fiber 23, in accordance with another embodiment of the present disclosure. FIG. 16B illustrates exemplary measurements for the components of the tester device 1300. In one example, a diameter of the optical fiber bundle head 53 portion of the tester device 1300 is approximately 5.5 mm. In the example, the copper tube 5a portion is approximately 1.0 mm in diameter with a central hollow portion (e.g., a center hole) of approximately 0.5 mm in diameter. Other approximate exemplary measurements are illustrated in FIG. 16B.

FIG. 17A is cross-sectional view of the probe 4a and an optical fiber bundle assembly, in accordance with another embodiment of the present disclosure. The probe 4a includes the probe tip 5 and the optical fiber 23. The optical fiber bundle assembly includes the optical fiber bundle head 53, the optical fiber bundle legs 54, and the optical fiber bundle 59. FIG. 17B is a cross sectional view of the tip 5 of the probe 4a and the optical fiber bundle head 53, in accordance with another embodiment of the present disclosure. FIG. 17B further illustrates a cross section of the tip 5 of the probe 4a taken at line A-A and shows exemplary dimensions of the tip 5 (a diameter of the copper tube 5a) and the optical fiber 23.

FIG. 17C is an isometric view illustrating dimensions of the copper tube 5a with the thermistor 25 of the apparatus 1300, in accordance with another embodiment of the present disclosure. The copper tube 5a is heated during the start-up of the apparatus 1300 (warming-up) and continuously being heated during idle and thermal conductivity testing. The copper tube 5a may be always heated and may be ready for testing a gemstone. The heating element 24 and the thermistor 25 are attached on the copper tube 5a. In some embodiments, the heating element 24 and the thermistor 25 are locked by glue and rolled over by connecting (magnetic) wires 26 to lock in place. The shrinkable tube 34 is utilized to isolate the heating element 24 and the thermistor 25 from the copper tube 5a to prevent short circuit. The heating element 24 and the thermistor 25 are coupled to the MCU 36 by way of the connecting wires 26 to control and monitor the temperature of the copper tube 5a, for maintaining the stability of the desired temperature. In the thermal conductivity test of the apparatus 1300, the temperature of the gemstone under test is not being measured but rather the amount of heat transfer from the copper tube 5a to the gemstone 12 or 13 is determined. The amount of heat transferred is determined by measuring the voltage difference of the two wires, one that is soldered on the copper tube 5a with 4-5 mm distance from the heating element 24 and the other wire that is soldered near the thermistor 25 at the opposite side of the copper tube 5a. In FIG. 17C, the two soldered connections are shown at either end of the shrinkable tube 34. The measured voltage difference may be amplified by the OP-AMP 37 and an output of the OP-AMP 37 is measured by the MCU 36. The measured output of the OP-AMP 37 is utilized for thermal conductivity testing, to measure the amount of heat transfer from the copper tube 5a to the gemstone 12 or 13.

FIGS. 18A-18C, collectively, represent a flow chart 1800 illustrating a mode of operation of the apparatus 1300 for gemstone testing, in accordance with another embodiment of the present disclosure.

Referring now to FIG. 18A, upon powering on the apparatus 1300 by way of the power switch 3 and initialization of the apparatus 1300, at 1801, the copper tube 5a is heated by the heating element 24 and the temperature of the copper tube 5a is sensed by the thermistor 25 until it reaches the desired temperature for testing. At 1802, successful warm-up of the copper tube 5a is determined. If in the case of failure in warming-up (e.g., if the warming-up of the copper tube 5a is unsuccessful), at 1803, an "Error Code" is generated and displayed on the touch screen display panel 6a to indicate an error in the initialization of the apparatus 1300, and the apparatus 1300 may proceed to shut down (1812). After the successful warm-up, at 1804, the auto-calibration of the probe 4a is performed. At 1805, the calibration data is received which is stored in a memory card such as an SD Card. The tester device 1300 calibrates itself using the stored calibration data. At 1806, successful calibration of the probe 4a is determined. If in the case of failure in calibration (e.g., if the calibration of the tester device 1300 is unsuccessful), at 1807, an "Error Code" is generated and displayed on the touch screen display panel 6a to indicate an error in the initialization of the apparatus 1300, and the apparatus 1300 may proceed to shut down. If the calibration is successful, at 1808, a ready signal is sent to the speaker 7 and the touch screen display panel 6a to output audio information "Ready" and display "Ready" on the touch screen display panel 6a to indicate that the apparatus 1300 is ready for testing.

Referring now to FIG. 18B, once the ready signal has been sent, the user may initiate the testing process by making contact between the probe tip 5 and the gemstone under test. At 1809, the force sensor 60 senses a force applied by the user while making the contact with the gemstone. Once the force sensor 60 senses a force, a force signal is sent to the MCU 36 by the force sensor 60 to trigger the testing process. Once the force signal has been sent, testing may be enabled. At 1810, enabling of testing is determined. If testing is not enabled, the apparatus 1300 may enter standby mode or sleep mode. At 1811, the apparatus 1300 determines whether a time period of the apparatus being in the standby mode is greater than a sleep threshold. If the time period of the apparatus being in the standby mode is less than the sleep threshold, 1809 is executed again. If the time period of the apparatus being in the standby mode is greater than the sleep threshold, the apparatus 1300 enters sleep mode, and at 1812, the apparatus 1300 shuts down. If testing is enabled, at 1813, a test sequence may begin and "Testing" is displayed on the touch screen display panel 6a to indicate that the apparatus 1300 is performing testing of the gemstone.

In one embodiment, before testing of the gemstone begins, at 1814, the apparatus 1300 detects using electrical conductivity testing that the probe tip 5 has not been placed in contact with a metal. In a scenario, the probe tip 5 may be placed in contact with the metal, when testing a gemstone (which has a high thermal conductivity) is mounted on a metal jewelry. The common material used to hold a jewelry stone is metal which has a high electrical conductivity. To be able to detect whether the probe 4 touches a metal or Natural Diamond or Synthetic Diamond, the metal is detected by the electrical conductivity test.

A simple thermal conductivity test may not be able to separate Diamond, Synthetic, Moissanite, CVD/HPHT from metal because all of these materials have high thermal conductivity. To separate high thermal conductivity stones from metal using a simple method, a simple electrical conductivity test is performed. To perform the electrical conductivity test, the apparatus 1300 detects whether there is a closed loop circuit between these following parts and objects: the internal metal detect circuit (inside the apparatus 1300) including the metal detector contact spring 49, the conductive hand grip 8, two hands 10 of the user (use left and right to hold apparatus and stone holder), conductive stone holder (for mounted setting, e.g., the metal ring 11) or conductive stone tray (for loose settings, e.g., the metal tray 14), the object being touched by test probe (test object), and the test probe 4. The internal metal detect circuit has a pull-up resistor while the other end of the test probe 4 is connected to circuit ground, this makes a closed-loop circuit when the object touched by test probe 4 is a conductive material like metal. The internal metal detect circuit is further coupled to the MCU 36 for detecting changes in output. If a low voltage amplitude (closed-loop circuit) is detected, a metal is detected, and an alarm may be triggered with visual and audio indications. If a high voltage amplitude (open-loop circuit) is detected, a non-metal is detected, and the process may proceed with further testing such as thermal conductivity and UV reflectivity tests.

The apparatus 1300 for the electrical conductivity material test includes the hand grip 8 which is internally coupled to the electronics circuit, e.g., the metal detector contact spring 49, and outwardly coupled to the user's hand 10. The apparatus 1300 detects the metal by a closed loop conductivity test with the use of both hands 10 of the user. In the case of testing loose stones, the gemstone 13 may be placed on the slot of the provided metal tray 14 and the user may hold the apparatus at the conductive hand grip 8 with one hand and the other hand on the metal tray 14. If the probe 4 is in contact with an electrically conductive material, at 1815, a reading is generated and corresponding data (data1) is stored in temporary or permanent memory. At 1816, the apparatus 1300 determines whether metal is detected. If metal is detected, at 1817, a metal alert signal is sent to the speaker 7 and the touch screen display panel 6a to output audio information "Metal Alert" and display "Metal Alert" to indicate that the metal is detected by the apparatus 1300 and perform step 1810 again. After this alert, the user may reposition the probe tip 5 to move the probe tip 5 away from the metal (such as in a jewelry setting) and onto the gemstone mounted on the jewelry. By adjusting the location of the probe 4a, the user may avoid the probe 4a touching the metal.

In some embodiments, when testing of the stone begins, the first test is an electrical conductivity test, the second test is a thermal conductivity test, and the third test is an optical test or lighting test. The same probe 4a and the probe tip 5 may be utilized for both the thermal conductivity test and the optical light test. Additionally, in some embodiments, the electrical conductivity test is performed with the same probe tip 5.

In some embodiments, at 1818, the thermal conductivity test is done by measuring the amount of heat transfer from the copper tube 5a to the gemstone 12 or 13. A small amount of voltage is amplified by the OP-AMP 37 and a voltage output of the OP-AMP 37 is measured by the MCU 36. When the testing starts, the voltage output from the OP-AMP 37 is increasing and the MCU 36 waits for the voltage output to be stable before obtaining a final reading. The final reading may be compared to the threshold values to determine if the thermal conductivity is in the low, medium, or high range. For example, a Limit 1, a Limit 2, a Limit 3, and a Limit 4 represent the voltage levels. If the reading is low (between the Limit 1 to the Limit 2) the testing result is Cubic Zirconia, if the reading is medium (between the Limit 2 to the Limit 3) the testing result is Simulant, and if the reading is high (greater than the Limit 3 or between the Limit 3 and the Limit 4) the testing result is for Natural Diamond, Synthetic Diamond (CVD/HPHT), and Moissanite. Based on which data matches or seems closest, the MCU 36 determines the type of specimen under test (e.g., cubic zirconia or simulant). Finally, if the value is low to medium, there is no need to proceed of the optical testing, while if the value is high, the next process is to perform the optical testing to separate the Natural Diamond from CVD/HPHT Diamond and Moissanite as all these stones may not be separated by the thermal conductivity testing.

In some embodiments, an impulse of thermal power is applied to the gemstone by contact with the flat surface or head and the resulting change in resistance of the thermistor 25 is sensed. The thermal power or heat is supplied by the heating element 24, for example a heating resistor. The change in resistance is weighted by a sensed resistance to give an indication of change in temperature. In some embodiments, a sensor such as the thermistor 25 is used for heat sensing. Using thermal conductivity testing, based on the heat conductivity of the specimen being tested the MCU 36 determines whether the specimen is cubic zirconia or a simulant. Each of the cubic zirconia and the simulant have different thermal conductivity properties as described above. At 1819, the MCU 36 receives data (data 2). The MCU 36 compares the data to the limits accessed regarding the thermal conductivity of different types of possible specimens (for example cubic zirconia and simulants thermal conductivity related data). Based on which data matches or seems closest, the MCU 36 determines the type of specimen (e.g., cubic zirconia or simulant). In some embodiment, the amount of heat conductivity sensed is measured by the apparatus 1300. In some embodiment, the heat conductivity is measured based upon the amount of time it takes for the heating element 24 to sense a cooling-off of a predetermined number of degrees (between two selected temperatures). It may be understood by a person skilled in the art that other methods of calculating the heat conductivity may be utilized, without deviating from the scope of the present disclosure. In some embodiments, at 1820, the MCU 36 determines whether the data 2 (e.g., the heat conductivity sensed) is between the Limit 1 and the Limit 2. If the data 2 is between Limit 1 and the Limit 2, the specimen is determined to be Cubic Zirconia. At 1821, "CZ" is displayed on the touch screen display panel 6a to indicate that the Cubic Zirconia is detected by the apparatus 1300, and 1810 is executed again. At 1822, the MCU 36 determines whether the data 2 is between the Limit 2 and the Limit 3. If the data 2 is between the Limit 2 and the Limit 3, the specimen is determined to be a simulant. At 1823, "SIMULANT" is displayed on the touch screen display panel 6a to indicate that the simulant is detected by the apparatus 1300, and 1810 is executed again. If the data 2 is greater than the Limit 3, the MCU 36 proceeds to optical testing, e.g., ultraviolet (UV) light testing.

Referring now to FIG. 18C, in some embodiments, the thermal conductivity testing is followed by optical intensity test. At 1824, the optical intensity testing is initialized. In some embodiments, the UV LEDs 56 are used for the optical intensity testing. The UV light is emitted towards the specimen by the optical fibers at the optical fiber bundle head 53 to strike and illuminate the specimen, preferably on the table facet of the specimen (e.g., the gemstone 12 or 13). The optical detector 52 is configured to detect the light that is reflected back from the specimen into the fiber optic 23 of the test probe 4a. In some embodiments, photodiodes are utilized in the optical detector 52 to detect light energy and generate a flow of current in an external circuit which is amplified in direct current (DC) by an amplifying circuit and transmitted to the processing unit for analyzing and processing. At 1825, a reading UVA and UVC is obtained of the intensity of light sensed which may be stored in temporary or permanent memory by the MCU 36.

As part of the UV intensity testing process, long wave lights and short wave lights may be used. In one embodiment, the longwave lights emitted by the UV LEDs 56 and radiated by the optical fiber bundle head 53 may be activated first. Once the optical detector 52 detects the longwave lights emitted by the optical fiber bundle head 53, the shortwave lights may be activated. The optical detector 52 may receive the short-wave lights and the MCU 36 may be configured to automatically control the testing process and the test result.

In one embodiment, in the UV intensity testing process, a photodiode is utilized in the optical detector 52 to detect light energy and generate a flow of current in an external circuit which is amplified in DC by an amplifying circuit. The amplifying circuit converts a variable input photocurrent in a form of analog light signals to a proportional voltage and transmit to the MCU 36 for analyzing and processing. The reading is obtained of the intensity of light sensed which is the voltage data may fall into one of the 3 categories. Category 1, UVA and UVC are LOW light intensity and the specimen is determined to be moissanite. At 1826, the MCU 36 determines whether UVA and UVC are Low light intensity. If UVA and UVC are Low light intensity, at 1827, "MOISSANITE" is displayed on the touch screen display panel 6a to indicate that the moissanite is detected by the apparatus 1300, and 1810 is executed again. Category 2, UVA & UVC are HIGH light intensity and the specimen is determined to be a CVD/HPHT, At 1828, the MCU 36 determines whether UVA and UVC are High light intensity. If UVA and UVC are High light intensity, at 1829, "CVD/HPHT" is displayed on the touch screen display panel 6a to indicate that the CVD/HPHT is detected by the apparatus 1300, and 1810 is executed again. Category 3, UVA is HIGH and UVC is LOW light intensity and the specimen is determined to be a Diamond. At 1830, the MCU 36 determines whether UVA is High and UVC is Low light intensity. If UVA is High and UVC is Low light intensity, at 1831, "DIAMOND" is displayed on the touch screen display panel 6a to indicate that the diamond is detected by the apparatus 1300, and 1810 is executed again. However, if the test results are outside the above categories, at 1832, an "Error Code" is generated and displayed on the touch screen display panel 6a to indicate an error in the testing process of the apparatus 1300, and 1810 is executed again.

More specifically, when the testing has been activated, longwave and shortwave UV reflected intensity are measured by an optical detector 52 and the detected signal is amplified by the OP-AMP 37. The output of the OP-AMP 37 is measured by the MCU 36. In one example, the longwave UV LED 56 turns ON for about 300 mS followed by the shortwave UV LED 56 with the same turn ON time and is measured by the optical detector 52 during their individual ON state. The UV light absorbed by the colorless gemstone is assessed by the optical detector 52 that is configured in the photovoltaic mode in the pre-amplifier stage of the signal conditioner circuit shown FIG. 20. The photovoltaic mode configuration converts a variable input photocurrent in the form of analog light signals to a proportional voltage. In one example, a pre-amplifier with a low pass filter is used for this purpose.

FIG. 19 is a schematic block diagram of the apparatus 1300, in accordance with another embodiment of the present disclosure. FIG. 19 depicts a user holding a ring 11 with a mounted stone 12 in one hand 10 and holding the handheld casing 2a of the apparatus 1300 at the conductive hand grip material 8 in the other hand. The copper tube 5a is shown with the probe tip 5 in direct contact with the table facet of the gemstone 12.

In this embodiment, the following parts (body apparatus) are shown in an operable configuration: the power source 1 (USB-C Power input), the power switch 3, the copper tube 5a, the touch screen display panel 6a, the speaker 7, the conductive hand grip material 8, the gemstone 12 mounter on the metal ring 11, the optical fiber 23, the heat control assembly including the heating element 24 and the thermistor 25, the MCU 36, the OP-AMP 37, the battery charging control 43, the VREG 44, the rechargeable battery 45, the SD card 46, the BT Module 47, the metal detector contact spring 49 (e.g., the internal metal detect circuit), the optical window 51, the optical detector 52, the optical fiber bundle head 53 in the shape of a ring (hereinafter also referred to as the optical fiber ring 53), the multi-wave length UV LEDs 56, the optical lens 57, and the force sensor 60.

In operation, the power supply, the rechargeable battery 45 or the power source 1, once turned ON by way of the power switch 3 activates the voltage regulator 44 and the MCU 36. The power source 1 is operably coupled with the battery charging control 43. The battery charging control 43 is configured to receive the power supply from the power source 1, charge the rechargeable battery 45, and monitor a charging level of the rechargeable battery 45. When the charging level of the rechargeable battery 45 is high, the battery charging control 43 discontinues charging of the rechargeable battery 45. The voltage regulator 44 is configured to generate 5V and 3.3V output and provide the generated output to the MCU 36, the SD Card 46, and the BT module 47. The SD Card 46 is configured to store audio files and calibration data, and is operably coupled to the MCU 36 to provide audio files associated with the selected language for indicating the testing and identification results. The BT Module 47 is operably coupled to the MCU 36 and is configured to communicate the testing and identification results to an external electronic device, such as smart phone or tablet, through a wireless communication network, such as Bluetooth. The MCU 36 is configured to control the testing and identification functions of the tester device 1300.

The user controls the device functions through a menu on the touch screen display panel 6a. The touch screen display panel 6a is operably coupled to the MCU 36. The optical fiber ring 53 is operably coupled to the optical lens 57 and the multi wavelength UV LEDs 56. The copper tube 5a is operably coupled to the heat control assembly including the heating element 24 and the thermistor 25 and an optical assembly including the optical window 51 and the optical detector 52. The multi wavelength UV LEDs 56 are operably coupled to the MCU 36.

The force sensor 60 is coupled with the MCU 36 and is configured to sense the contact of the probe tip 5 with the gemstone under test to trigger the testing process. The internal metal detect circuit is configured to prevent inaccurate testing. The internal metal detect circuit is coupled to the MCU 36 for detecting changes in output. If low voltage amplitude (closed-loop circuit) is detected, the metal is detected, and an alert is provided with audio by way of the speaker 7 and displayed by way of the touch screen display panel 6a.

The functional testing apparatus 1300 comprises the speaker 7, and the visual indicator 6a which is the touch screen display panel 6a that are operatively coupled to the MCU 36. Accordingly, once the test result is generated, a test result signal is generated by the MCU 36 and sent to the speaker 7, and the touch screen display panel 6a which displays the characters/names such as "DIAMOND", "CVD/HPHT", "MOISSANITE," "SIMULANT" and "CZ" in response to the test result signal sent from the MCU 36. The MCU 36 further comprises a Bluetooth communication unit operatively coupled to the BT Module 47 to transmit the test result to the functional unit and at the same time to transmit the test result to an external electronic device, such as smart phone or tablet. The BT module 47 transmits the test result to the external electronic device through a wireless communication network, such as Bluetooth.

From FIG. 19, the flow of an example of an operation sequence of the gemstone testing device may be explained. Once the power switch 3 is powered ON, the tester device 1300, using the MCU 36, is configured to self-calibrate through a software program. If the tester device 1300 is able to be properly calibrate, "Ready" may be displayed on the menu functions on the touch screen display panel 6a. After the display of "Ready," the apparatus 1300 is ready for testing. The sequence and flow of events of FIGS. 18A-18C follows for performing thermal, electrical, and optical testing of the gemstone under test.

FIG. 20 is a schematic diagram of a pre-amplifier circuit with a low pass filter, in accordance with an embodiment of the present disclosure. A relationship between the two variables a voltage photocurrent (Vipd) and a photocurrent (Ipd) is represented by the equation given below:

$$Vipd = Ipd(Rf + R1)$$

where:
Vipd is the voltage corresponding to the photocurrent,
Ipd is the photocurrent,
Rf is a feedback resistor, and
R1 is a resistor tied to the anode of the photodiode.

The apparatus 1300 performs thermal testing in a manner similar to the thermal testing performed by the apparatus 100 as described in FIG. 11B.

The disclosed embodiments encompass numerous advantages. The disclosure provides various methods and apparatus for testing and identifying gemstones. The disclosed methods and apparatus may facilitate several advantages for testing and identifying gemstones. Firstly, the apparatus provides a comprehensive and portable solution with a handheld case and probe, allowing for convenient and on-the-go gemstone analysis. In some embodiments, the probe is removable and replaceable. The incorporation of heating elements, thermistors, and optical fibers enables accurate measurement of heat transfer, as well as precise detection and measurement of reflected light from the gemstone. The use of UV LED sources and optical detectors facilitates the assessment of optical properties. The microcontroller's capabilities allow for simultaneous determination of multiple properties, including electrical, thermal, and optical characteristics, enabling efficient and holistic gemstone analysis. Photoconductivity effect may also be used. The visual indicator, which may be a touch screen display panel or multiple light sources, offers a clear and intuitive means of communicating the identified gemstone type. Additionally, the apparatus supports multilingual functionality and audio information output, enhancing user convenience and accessibility. The inclusion of a Bluetooth transceiver enables seamless communication with smartphones or tablets, expanding the device's capabilities and data management options. Overall, these features combine to provide a versatile, user-friendly, and technologically advanced gemstone testing and identification apparatus.

While various exemplary embodiments of the disclosed systems and methods have been described above, it should be understood that they have been presented for purposes of example only, and not limitations. It is not exhaustive and does not limit the disclosure to the precise form disclosed. Modifications and variations are possible in light of the above teachings or may be acquired from practicing of the disclosure, without departing from the breadth or scope.

While various embodiments of the disclosure have been illustrated and described, it will be clear that the disclosure is not limited to these embodiments only. Numerous modifications, changes, variations, substitutions, and equivalents will be apparent to those skilled in the art, without departing from the spirit and scope of the disclosure, as described in the claims.

Although the disclosure is described herein with reference to specific embodiments, various modifications and changes can be made without departing from the scope of the present disclosure as set forth in the claims below. Accordingly, the specification and figures are to be regarded in an illustrative rather than a restrictive sense, and all such modifications are intended to be included within the scope of the present disclosure. Any benefits, advantages, or solutions to problems that are described herein with regard to specific embodiments are not intended to be construed as a critical, required, or essential feature or element of any or all the claims.

The term "coupled," as used herein, is not intended to be limited to a direct coupling or a mechanical coupling.

Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to disclosures containing only one such element, even when the same claim includes the introductory phrases "one or more" or "at least one" and indefinite articles such as "a" or "an." The same holds true for the use of definite articles.

Unless stated otherwise, terms such as "first" and "second" are used to arbitrarily distinguish between the elements such terms describe. Thus, these terms are not necessarily intended to indicate temporal or other prioritization of such elements.

Unless otherwise stated, conditional languages such as "can", "could", "will", "might", or "may" are understood within the context as used in general to convey that certain embodiments include, while other embodiments do not include, certain features, elements and/or steps. Thus, such conditional languages are not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

It will be understood by those within the art that, in general, terms used herein, are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. An apparatus (100) for identifying precious stones and man-made stones, the apparatus comprising:
   a probe (4) comprising a metal tube (5a), at least one optical fiber (23) positioned within the metal tube (5a), and a tip (5) that makes contact with a flat surface of a stone (12, 13) under test, wherein the at least one optical fiber (23) is configured to receive light reflected from the stone under test;
   a handheld device (2) electronically coupled with the probe (4), wherein the probe (4) is removable and replaceable, the handheld device (2) comprising:
   a thermal testing assembly coupled to the metal tube (5a), and configured to provide heat to the metal tube and sense a temperature of the metal tube;

an optical assembly configured to generate at least one of a short wavelength UV light and a long wavelength UV light and illuminate the stone under test with at least one of the short wavelength UV light and the long wavelength UV light;
   an optical detector (52), wherein the optical detector (52) further comprises a photodiode configured to detect intensities of the short wavelength UV light and the long wavelength UV light reflected from the stone (12, 13) under test and generate a photocurrent;
   an amplifying circuit is configured to amplify the photocurrent and convert the amplified photocurrent into a proportional voltage signal;
   a microcontroller (36) operably coupled to the thermal testing assembly and the optical testing assembly, and configured to determine an amount of heat transfer from the metal tube (5a) to the stone under test (12, 13), determine at least one of: electrical properties, thermal properties, and optical properties of the stone under test, and identify a type of the stone under test based on the determined at least one of: the electrical properties, the thermal properties, and the optical properties,
   wherein the microcontroller (36) is configured to concurrently determine the electrical properties and the optical properties of the stone under test during a single measurement session,
   wherein the microcontroller (36) is further configured to receive the voltage signal and categorize the voltage signal into at least one of three categories: (a) both the long wavelength UV light and the short wavelength UV light intensities are low, indicating moissanite, or (ii) both the long wavelength UV light and the short wavelength UV light intensities are high, indicating CVD/HPHT, or (iii) the long wavelength UV light intensity is high and the short wavelength UV light intensity is low, indicating diamond; and
   a visual indicator (6) operably coupled to the microcontroller (36) and configured to indicate the type of the stone (12, 13) under test.

2. The apparatus (100) of claim 1, wherein:
the handheld device (2) further comprises a standardized connection (16),
the probe (4) further comprises a complementary standardized connection (17), and
the probe (4) is removably coupled to the handheld device (2) using the standardized connection (16) and complementary standardized connection (17).

3. The apparatus claim 2, wherein the standardized connection (16) is a female connection and the complementary standardized connection (17) is male connection, and wherein the probe (4) is adapted to be removed from the handheld device (2) without using any external tools.

4. The apparatus of claim 2, wherein the standardized connection comprises a universal serial bus (USB) connection.

5. The apparatus of claim 1, further comprising:
a detection switch (27) configured to detect a contact between the probe (4) and the stone under test (12, 13).

6. The apparatus of claim 5, wherein the detection switch (27) comprises one of an electronic mini-switch and a pressure sensitive sensor.

7. The apparatus of claim 5, wherein when the detection switch (27) detects the contact between the probe and the stone under test, and the at least one of the short wavelength UV light and the long wavelength UV light are generated.

8. The apparatus of claim 1, wherein the thermal testing assembly comprises:

a heating element (24) coupled to the metal tube, and configured to provide heat to the metal tube; and a thermistor (25) operably coupled to the metal tube, and configured to sense the temperature of the metal tube.

9. The apparatus of claim 1, wherein the optical testing assembly comprises:

a UV light emitting diode (LED) source (19) configured to generate at least one of the short wavelength UV light and the long wavelength UV light; and at least one optical fiber bundle optically coupled to the UV LED source, and configured to illuminate the stone (12, 13) under test with at least one of the short wavelength UV light and the long wavelength UV light, wherein an optical lens (57) is configured to couple light from the UV LED source into an optical fiber bundle leg (54), wherein the optical lens (57) is a ball lens that is placed between the optical fiber bundle leg (54) and the UV LED source, and wherein the ball lens allows light to travel between the UV LED source and the optical fiber bundle leg (54) with minimal losses.

10. The apparatus of claim 1, further comprising:

conductive hand grip (8) coupled to the handheld device (2), wherein the microcontroller (36) is further configured to determine whether the stone under test is a metal by using the conductive hand grip and the probe to determine a closed electrical circuit, thereby indicating an electrical conductivity of the stone under test.

11. The apparatus of claim 1, wherein a photoconductivity effect is used to determine the electrical properties of the stone under test the apparatus further comprises:

a set of relays (39, 40) and a voltage multiplier (42) coupled with the microcontroller (36), and configured to perform high voltage electrical conductivity testing on the stone under test;

wherein the optical assembly emits the at least one of the short wavelength UV light and the long wavelength UV light during the high voltage electrical conductivity testing.

12. The apparatus of claim 1, wherein:

the visual indicator (6) includes a plurality of light sources, and a single light source of the plurality of light sources is configured to represent more than one type of stone.

13. The apparatus of claim 1, further comprising:

a speaker (7) coupled with the microcontroller (36) and configured to output audio information, wherein the microcontroller is further configured to select a language for outputting the audio information on the speaker; and a Bluetooth transceiver (47) coupled to the microcontroller (36) and configured to communicate with a smartphone or a tablet via Bluetooth.

14. A method for identifying precious stones and manmade stones using a handheld testing apparatus (100), the method comprising:

using a probe (4) connected to the handheld testing apparatus;

heating a metal tube (5a) using a heating element (24) of the handheld testing apparatus;

sensing a temperature of the metal tube using a thermistor (25) of the handheld testing apparatus;

placing the heated metal tube in contact with a stone (12, 13) under test;

determining, using a microcontroller (36) of the handheld testing apparatus, an amount of heat transfer from the metal tube to the stone under test;

generating at least one of a short wavelength ultra-violet (UV) light and a long wavelength UV light;

illuminating the stone under test with at least one of the short wavelength UV light and the long wavelength UV light;

detecting, using a photodiode of an optical detector (52), intensities of the short wavelength UV light and the long wavelength UV light reflected from the stone under test (12, 13) and generating a photocurrent;

amplifying, using an amplifying circuit, the photocurrent and converting the amplified photocurrent into a proportional voltage signal;

concurrently determining, using the microcontroller, the electrical properties and the optical properties of the stone under test during a single measurement session;

identifying a type of the stone under test based on the determined at least one of: the electrical properties, the thermal properties, and the optical properties, receiving, using the microcontroller (36), the voltage signal and categorizing the voltage signal into at least one of three categories: (is) both the long wavelength UV light and the short wavelength UV light intensities are low, indicating moissanite, or (ii) both the long wavelength UV light and the short wavelength UV light intensities are high, indicating CVD/HPHT, or (iii) the long wavelength UV light intensity is high and the short wavelength UV light intensity is low, indicating diamond; and indicate the type of the stone under test by a visual indicator (6).

15. The method of claim 14, wherein the connected probe is removably coupled to the handheld testing apparatus using a standard connection, and wherein the probe is adapted to be removed from the handheld testing apparatus without using any external tools.

16. The method of claim 14, further comprising:

detecting a contact between the probe and the stone under test using a detection switch.

17. The method of claim 14, further comprising:

determining whether the stone under test is a metal by using a conductive hand grip and a probe of the handheld testing apparatus to determine a closed electrical circuit, thereby indicating an electrical conductivity of the stone under test.

18. The method of claim 14, determining the electrical properties of the stone under test using photoconductivity effect further comprises:

performing high voltage electrical conductivity testing on the stone under test, while the illuminating step is occurring, wherein the thermal properties, and either the optical properties or the electrical properties of the stone under test are determined concurrently.

19. The method of claim 14, wherein the stone under test is one of an earth-mined diamond, a Type IIa HPHT diamond, a Type IIa CVD diamond, a Simulant, a Moissanite, glass, cubic zirconia, emerald, tanzanite, garnet, tourmaline, jade, spinel, ruby and sapphire.

20. The apparatus of claim 1, wherein the microcontroller is further configured to concurrently determine the thermal properties of the stone under test together with the electrical properties and the optical properties during the single measurement session.

21. The apparatus of claim 1, wherein the metal tube comprises copper.

22. An apparatus for identifying precious stones and man-made stones, the apparatus comprising:

a probe comprising a metal tube and a tip that makes contact with a flat surface of a stone under test,;

a handheld device, electronically coupled with the probe, comprising:

a thermal testing assembly coupled to the metal tube and configured to provide heat to the metal tube and sense a temperature of the metal tube;

a high-voltage electrical conductivity testing assembly configured to apply a high-voltage signal to the stone under test and detect electrical conductivity of the stone under test;

a microcontroller operably coupled to the thermal testing assembly and the high-voltage electrical conductivity testing assembly, and configured to perform a sequential gemstone testing process comprising:

determine a thermal conductivity value of the stone under test; and perform a high-voltage electrical conductivity test only when the determined thermal conductivity value exceeds a predefined threshold value; and a visual indicator operably coupled to the microcontroller and configured to indicate the type of the stone under test.

23. The apparatus of claim 22, wherein during the high-voltage electrical conductivity test, the microcontroller is configured to induce a photoconductivity effect by activating a UV light source to illuminate the stone under test.

24. The apparatus of claim 22, wherein the microcontroller is configured to determine the thermal conductivity value of the stone under test by measuring a rate of heat transfer from the metal tube to the stone under test.

\* \* \* \* \*